United States Patent [19]
Kridl et al.

[11] Patent Number: 5,608,152
[45] Date of Patent: *Mar. 4, 1997

[54] SEED-SPECIFIC TRANSCRIPTIONAL REGULATION

[75] Inventors: Jean C. Kridl; Vic C. Knauf, both of Davis, Calif.

[73] Assignee: Calgene, Inc., Davis, Calif.

[*] Notice: The term of this patent shall not extend beyond the expiration date of Pat. No. 5,420,034.

[21] Appl. No.: 453,924

[22] Filed: May 30, 1995

Related U.S. Application Data

[62] Division of Ser. No. 742,834, Aug. 8, 1991, Pat. No. 5,420,034, which is a continuation of Ser. No. 550,804, Jul. 9, 1990, which is a continuation-in-part of Ser. No. 147,781, Jan. 25, 1988, abandoned, which is a continuation-in-part of Ser. No. 78,538, Jul. 28, 1987, abandoned, which is a continuation-in-part of Ser. No. 891,529, Jul. 31, 1986, abandoned.

[51] Int. Cl.$^6$ .......................... C12N 15/00; C12N 15/82
[52] U.S. Cl. .................. 800/205; 800/250; 800/255; 800/DIG. 17; 435/320.1; 435/172.3; 536/24.1; 935/22; 935/30; 935/67
[58] Field of Search ..................... 800/805, 250, 800/255; 435/172.3, 240.4, 320.1; 536/24.1, 27; 935/22, 30, 67

[56] References Cited

U.S. PATENT DOCUMENTS

| | | | |
|---|---|---|---|
| 4,764,061 | 9/1988 | Comai et al. | 71/86 |
| 4,886,753 | 12/1989 | Mareber et al. | 435/172.3 |

FOREIGN PATENT DOCUMENTS

| | | | |
|---|---|---|---|
| 0142924 | 5/1985 | European Pat. Off. | C12N 15/00 |
| 0193259 | 3/1988 | European Pat. Off. | 435/172.1 |
| 85/04899 | 11/1985 | WIPO | C12N 15/00 |
| 89/07299 | 12/1987 | WIPO | C12N 15/00 |

OTHER PUBLICATIONS

Barton et al., *Plant Physiol.* (1987) 85: 1103–1109.
Beachy et al., *EMBO J.* (1985) 4:3047–3053.
Chen et al., *Proc. Natl. Acad. Sci.* (1986) 83:8560–8564.
Crouch et al., *Mol. Form and Function of the Plant Genome* (1985), "Storage Protein mRNA Levels Can Be Regulated by Abscisic Acid in Brassica Embryos", pp. 555–566.
Crouch et al., *J. Molec. & Applied Genet.* (1983) 2:273–283.
Crouch et al., *Planta* (1981) 153:64–74.
Eckes et al., *Mol. Gen. Genet.* (1986) 205: 14–22.
Facciotti et al., *Biotechnology* (1985) 3:241–246.
Fluhr et al., *Science* (1985) 232:1106–1112.
Goldberg, R., *Cell* (1989) 56: 149–160.
Goodman et al., *Science* (1987) 236:48–54.
Greenwood et al., *Plant Physiol.*(1985) 79:65–71.
Knauf et al., *J. Amer. Chem. Soc.* (1987) 64:633.
Kuo et al., *Archives of Biochem. & Biophys.* (1984) 234:290–296.
Murray et al., *Z. Pflanzenphysiol.* (1983) 110:7–16.
Ohlrogee et al., *Chem. Abstracts* (1986) 105:55584k.
Padgett et al., *Ann. Rev. Biochem.* (1986) 55: 1119–1150.
Radke et al., *Commonwealth Agric. Bureau* (1986), abst. No.:CAB 881669878.
Rose et al., *Nucleic Acids Res.* (1987) 15: 7197.
Scherer et al., *Plant Molec. Biol.* (1987) PLAN 0043: 1–8.
Scofield et al., *J. Cell Biochem. Suppl.2* (1985) 9C: 1695.
Scofield et al., *J. Biol. Chem.* (1987) 25: 12202–12208.
Sengupta–Gopalan et al., *Proc. Natl. Acad. Sci. USA* (1985) 82:3320–3324.
Simon et al., *Plant Molecular Biol.* (1985) 5: 191–201.
Vasil et al., *Biotechnology* (1988) 6:397–402.
Willmitzer, L., *Trends in Genet.* (1988) 4: 13–18.

Primary Examiner—Gary Benzion
Attorney, Agent, or Firm—Rae-Venter Law Group P.C.

[57] ABSTRACT

Brassica plants and seeds comprising nucleic acid sequences and methods for their use are provided which afford seed-specific transcription in order to modulate or modify expression in seed particularly in embryo cells. Transcriptional initiation regions are identified and isolated from plant cells such as seed embryo and seed coat and used to prepare expression cassettes which may then be transformed into plants cells for seed specific transcription. The method finds particular use in conjunction with modifying fatty acid production in seed tissue.

14 Claims, 25 Drawing Sheets

```
                                                       Sau3AI    AluI
                                                         ┤        ┤
                                                       1156     1166
1105 CATAGGAGGTGGGAGAATGGGTATAGAATAACATCAATGGCAGCAACTGCGATCAAGCAGCTTTCATA 1173

HinfI
                                        ┤
                                      1216
1174 TTAAGCATACCAAAGCGTAAGATGTGGATGAAACTCAAGAGACTCTCCGCACCACCGCCTTTCCAAGT 1242

ScaI                        AluI                    Sau3AI
     RsaI                          ┤                       ┤
      ┤                          1269                    1286
     1243
     1243
1243 ACTCATGTCAAGGTTGGTTTCTTTAGCTTTGAACACAGATTTGGATCTTTTTGTTTTGTTTCCATATAC 1311

DdeI
     AvaII AluI                                         HinfI    RsaI
      ┤    ┤                                              ┤       ┤
     1316 1326                                          1368    1375
     1320
1312 ATAGGACCTGAGAGCTTTTGGTTGAATTTTTTTTTTCAGGACAAATGGGCGAAGAATCTGTACATTG 1380

1381 CATCAATATGCTATGGCAGGACAGTGTGCTGATGATACACACTTAAGCATCATGTGTTGTGTTAGAAAG 1449

MstII                                                 Tth111I
              DdeI                                                    ┤
              ┤                                                     1514
             1472
             1472
1450 CCGAAGACAATTGGAGCGAGCCTCAGGGTCGTCATAATACCAATCAAAGACGTAAAACCAGCGCAGTC 1518
```

FIG. 1D

Lambda CGN1-2
NCG-186 Linear    LENGTH = 4325

```
        XhoI                                        HindIII
        TaqI                                        AluI        TaqI
        AvaI                                         ¦           ¦
         ¦¦¦                                         ¦           ¦
  1 CTCGAGGCAGTCACTAACATGAAGTTTGACGAGGAGCCCAACTATGGGAAGCTTATTCTCTTTTCGAT   69
    2 3                                            50 52        66
    2

HhaI XbaI                               SacI
                   ¦   ¦                                 AluI
                   ¦   ¦                                  ¦ ¦
 70 ACTCTAATTGAGCCGTGCGCTCTATCTAGACCAATTAGAATTGATGGAGCTCTAAAGGTTGCTGGCTGT  138
                  89  95                                119
                                                          121

NdeI                                                      NdeI
         ¦                                                         ¦
139 TTCTTGTTCATATGATTAACTTCTAAACTTGTGTATAAATATTCTCTGAAAGTGCTTCTTTTGGCATA  207
           150                                                    206

Sau3AI
                            DdeI
                             ¦¦
208 TGTAGGTTGGGCAAAAACGAGGAAGAGATTGCTTCTCAATTTGGAAGAGAGGATGAACAGCCGAAGAAGAAAA  276

277 TAAGAATAGGCAGTCCTGCTACTCAATGGATCTCAGTCTATAACGGTCGTCGTCCCATGAAACAGAGGT  345
                                    305 309

EcoRV
                                                    ¦
346 AAAACATTTTTTGCATATACACTTTGAAAGTTCCTCACTAACTGTGTAATCTTTTGGTAGATATCACTA  414
                                                    408
```

```
                    HincII
                    HhaI
                    HaeIII
                    DdeI
                    BstEII
                    BalI
                    |||                      HaeIII      AluI
                                              |-|         |-|
415 CAATGTCGGAGAGACAA3GGCTGMNCANCATATACAAAAGGGAAATGAAGATGGCCTTTTGATTAGCTG 483
                    439                              469        481
                    438
                    439
                    439
                    440
                    438

AluI                     HinfI
            |-|                       |-|
484 TGTAGCATCAGCAGCTAATCTCTGGGCTCTCATCATGGATGCTGGAACTGGATTCACTTCTCAAGTTTA 552
            498                              535

MspI                                            HinfI
    HpaII                                            |-|
    |-|
553 TGAGTTGTCACCGGTCTTCCTACACAAGGTAATAATCAGTTGAAGCAATTAAGAATCAATTTGATTTGT 621
    564                                              606
    564
DdeI 622 AGTAAACTAAGAAGAACTTACCTTATGTTTTCCCGCAGGACTGGATTATGGAACAATGGGAAAAGAAC 690
    629

SacI
           AluI    AluI                               AluI
            |-|     |-|                                |-|
691 TACTATATAAGCTCCATAGCTGGTTCAGATAACGGGAGCTCTTTAGTTGTTATGTCAAAAGGTTAGTGT 759
    702     710                                       729
                                                        731
```

```
                                                      DdeI       HinfI
760  TTAGTGAATAATAAACTTATACCACCAAAGTCTTCATTGACTTATTATATACTGTTGTGAATTGCTAG 828
                                |                   |
                               842                 865
         XmnI                                                              TaqI
829  GAACTACTTATTCTCAGCAGTCATACAAAGTGAGTGACTCATTCCGTTCAAGTGGATAAATAAGAAAT 897
                                                                           |
                                                                          961
       Sau3AI
       BclI
898  GGAAAGAAGAGATTTTCATGTAACCTCCATGACAACTGCTGGTAATCGTTGGGGTGTGGTAATGTCGAGGA 966
       |
      908
                                                   AluI   RsaI
967  ACTCTGGGCTTCTCTCTGATCAGGTAGGTTTTTGTCTCTTATTGTCTGGTGTTTTATTTCCCCTGATAGT 1035
                                                   |      |
                                                  981    981
                                                               1074   1087
1036 CTAATATGATAAACTCTGCGTTGTGAAAGGTGGTGGAGCTTGACTTTTGTACCCAAGCGATGGGATAC 1104
                                                        Sau3AI AluI
1105 ATAGGAGGTGGGAGAATGGGTATAGAATAACATCAATGCAGCAACTGCGGATCAAGCAGCTTTCATAT 1173
                                                        |      |
                                                       1155   1165
                                                                      ScaI
                                                                      RsaI
                                         HinfI                        |
1174 TAAGCATACCAAAGCGTAAGATGGTGGATGAAACTCAAGAGACTCTCCGCACCACCGCCTTTCCAAGTA 1242
                                          |                          1242
                                         1215
```

FIG. 2C

```
                              AluI        Sau3AI                                    DdeI
1243 CTCATGTCAAGGTTGGTTTCTTTAGCTTTGAACACAGATTTGGATCTTTTGTTTTGTTTCCATATACT 1311
                               1268          1285                                   1311

DdeI
       AvaI|  AluI                                       HinfI  RsaI
        | |   |                                            |      |
1312 TAGGACCTGAGAGCTTTTGGTTGATTTTTTTTCAGGACAAATGGGGCGAAGAATCTGTACATTGCATCA 1380
       1315 1319 1325                                   1363    1370

1381 ATATGCTATGGCAGGACAGTGTGCTGATACACACTTAAGCATCATGTGGAAAGCCAAAGACAATTGGAG 1449

HinfI
        |
        DdeI
         |
1450 CGAGACTCAGGGTCGTCGTCATAATACCAATCAAAGACGTAAAACCAGAGCGCAACCTCTTTGGTTGAATGTA 1518
                    1454
                    1456

RsaI
                                          |
1519 ATGAAAGGGATGTGTCTTGGTATGTATGTACGAATAACAAAGAGAAGATGGAATTAGTAGTAGAAATA 1587
                                        1548

AluI                                EcoRV
             |                                    |
1588 TTTGGGAGCTTTTTAAGCCCTTCAAGTGTGCTTTTATCTTATTGATATCATCCATTGCGTTGTTAA 1656
                  1596                                       1635

XbaI                DdeI
         |                   |
1657 TGCGTCTCTAGATATGTTCCTATATCTTTCTCAGTGTCTGATAAGTGAAATGTGAGAAAACCATACCAA 1725
          1664               1687
```

```
                                                  HinfI
1726 ACCAAAATATTCAAATCTTATTTTAATAATGTTGAATCACTCGGAGTTGCCACCTTCTGTGCCAATTG 1794

HinfI                                                          EcoRI
1795 TGCTGAATCTATCACACTAGAAAAAAAAACATTTCTTCAAGGTAATGACTTGTGGACTATGTTCTGAATTC 1863
                        1800                                    1859

1864 TCATTAAGTTTTTATTTTCTGAAGTTTAAGTTTTACCTTTCTGTTTTGAAATATATCGTTCATAAGATG 1932
                                                    SphI
      BstNI   AluI                                  Sau3AI
1933 TCACGCCAGGACATGAGCTACACACATGCACATAGCATGCAGATCAGGACGATTGTCACTCACTTCAAA 2001
              1940    1950                             1971
                                                       1973
      DdeI AluI        HhaI   NdeI NsiI           SphI      Sau3AI
2002 CACCTAAGAGAGCTTCTCTCTCACAGGCGCACACACATGCAATATTTACACGTGATCGCCATGCAA 2070
      2006  2012        2028     2036 2042                2058
                                      2044

2071 ATCTCCATTCTCACCTATAAATTAGAGCCTCGGCTTCACTCTTTACTCAAACCAAAACTCATCACTACA 2139
                AluI
2140 GAACATACACAAATGGCGAACAAGCTCTTCCTCGTCTCGGCAACTCTGCCTTGTTCTTCCTTCTCACC 2208
                  METAlaAsnLysLeuPheLeuValSerAlaThrLeuAlaLeuPhePheLeuLeuThr
                  2164
```

FIG. 2F

```
                                                      NaeI
                                                      MspI
                                           TaqI       HpaII
                                           SalI        HaeIII
                                           HincII       ‖
                                           AccI         ‖
         AccI                               ‖‖‖
          I                                 ‖‖‖
2209 AATGCCTCCGTCTACAGGACGGTTGTGTGGAAGTCGACGAAGATGATGCCACAAATCCAGCCGGCCCATTT 2277
     AsnAlaSerValTyrArgThrValValGluValAspGluValAspAspAlaThrAsnProAlaGlyProPhe
                                         2220                  2239   2268 2271
                                                                 2240 2268
                                                                 2241 2269

HindIII
                                                    AluI
         HinfI                                       ‖
          I                                          ‖
2278 AGGATTCCAAAAATGTAGGAAGGAGTTTCAGCAAGCACAACACCTGAAAGCTTGCCAACAATGGCTCCAC 2346
     ArgIleProLysCysArgLysGluPheGlnGlnAlaGlnHisLeuLysAlaCysGlnTrpLeuHis
           2281                                                2325
                                                               2327

MspI         AvaII
                   HpaII AvaII  AluI   TaqI
                    ‖      I     I      I
2347 AAGCAGGCAATGCAGTCCGGTAGTGGTCCAAGCTGGTGGACCCTCGATGGTGAGTTTGATTTTGAAGACGAC 2415
     LysGlnAlaMETGlnSerGlySerGlyProSerTrpTrpThrLeuAspGlyGluPheAspPheGluAspAsp
                         2364 2372         2379 2382 2388
                         2364

HaeIII
             ApaI              HaeIII                              SacI
              I                  I                                 AluI
              ‖                  ‖                                  ‖
2416 GTGGAGAACCAACAACAGGGCCCGCAGAGGCCCAGAGGCTGCTCCAGCAGTGCTGCAACGAGCTCCAC 2484
     ValGluAsnGlnGlnGlnGlyProGlnArgProGlnArgLeuLeuGlnGlnCysCysAsnGluLeuHis
                         2436                    2449                 2479
                         2438                                         2481

TaqI
                                                                 HinfI
         BstNI                                                    I
          I                                                       ‖
2485 CAGGAAGAGCCACTTTGCGTTTGCCAACCTTGAAAGGAGCATCCAAAGCCGTTAAACAACAGATTCGA 2553
     GlnGluGluProLeuCysValCysProThrLeuLysGlyAlaSerLysAlaValLysGlnIleArg
      2486                                                    2548
                                                              2551
```

FIG. 2G

```
2554 CAACAACAGGGACAACAAATGCAGGGACAGCAGCAAGTGATTAGCCGTATCTACCAGACCGCT 2622
      GlnGlnGlnGlyGlnGlyGlnGlyGlnMETGlnGlnValIleSerArgIleTyrGlnThrAla
                        AluI                                    BstNI
                         |                                        |
2623 ACGCACTTACCTAGAGCTTGCAACATCAGGCAAGTTAGCATTTGCCCCTTCCAGAGACCATGCCTGGG 2691
      ThrHisLeuProArgAlaCysAsnIleArgGlnValSerIleCysProPheGlnLysThrMETProGly
                                                                   2688
         MspI                          XhoI
         HpaII                          TaqI
         HaeIII        HinfI           AvaI          AccI
          ApaI         |                |             |
           |
2692 CCCGGCTTCTACTAGAGATTCCAAACGAATATCCTGAGAGTGTGTATACCACGGTGATATGAGTGTGGTT 2760
      ProGlyPheTyr        2707                 2724         2736
         2694                                  2725
         2692                                  2724
         2694
         2694
                 HincII
                   |
2761 GTTGATGTATGTTAACACTACATAGTCATGGTGTGTGTTCCATAAATAATGTACTAATGTAATAAGAAC 2829
                     2771                                         2813
           AccI                                    RsaI
            |                                        |
2830 TACTCCGTAGACGGTAATAAAAGAGAAGTTTTTTTTTTTTACTCTTGCTACTTCCTATAAAGTGATGAT 2898
              2838
                                                                  ScaI
                                                                  RsaI
                                                                   |
2899 TAACAACAGATACACCCAAAAAGAAAAACAATTAATCTATATTCACAATGAAGCAGTACTAGTCTATTGAA 2967
                                                                    2954
                                                                    2954
```

```
                                                                Sau3AI
                                                                  |
2968 CATGTCAGATTTCTTTTTCTAAATGTCTAATTAAGCCTTCAAGGCTAGTGATGATAAAGATCATCCA 3036
                                                                     3028

Sau3AI           Sau3AI
     BamHI   HinfI    BclI
       |      |        |
3037 ATGGGATCCAACAAAGACTCAAATCTGGTTTTGATCAGATACTTCAAAACTATTTTGTATTCATTAAA 3105
        3041          3069
        3041   3053   3069
                          HinfI
                            |
3016 TTATGCAAGTGTTCTTTTATTTGGTGAAGACTCTTTAGAAGCAAAGAACGACAAGCAGTAATAAAAAA 3174
                                           3135

3175 ACAAAGTTCAGTTTAAGATTTGTTATTGACTTATTGTCATTTGAAAAATATAGTATGATATTAATATA 3243

3244 GTTTATTTATATAATGCTTGTGTCTATTCAAGATTTGAGAACATTAATATGATACTGTCCACATATCCAA 3312
                                             NdeI
                                              |
3313 TATATTAAGTTTCATTTCTGTCAAACATATGATAAGATGGTCAAATGATTATGAGTTTTGTTATTTAC 3381
                                       3341
              TaqI      Sau3AI
           AluI    RsaI   |
            |  |    |
3382 CTGAAGAAAAGATAAGTGAGCTTCGAGTTTCTGAAGGGTACGTGATCTTCATTTCTTGGCTAAAAGCGA 3450
           3402       3421
           3405       3425

3451 ATATGACATCACCTAGAGAAAAGCCGATAATAGTAAACTCTGTTCTTGGTTTTTGGTTTAATCAAACCGA 3519
```

```
              MspI  DdeI                              NdeI             HinfI      MspI
              HpaII AluI                                                          HpaII
              |    |                                  |                |          |
3520 ACCGGTAGCTGAGTGTCAAGTCAGCAAACATCGCAAACCATATGTCAATTCGTTAGATTCCCGGTTTAA 3588
              3522 3528                               3560             3576       3581
              3522 3529                                                           3581

MspI
              HpaII
              |
3589 GTTGTAAACCGGTATTTCATTTGGTGAAAACCCTAGAAGCCAGCCANCCTTTTAATCTAATTTTTGCA 3657
              3598
              3598

HinfI
                                                        HincII
                                                        BstNI
                                          DdeI          | |
                                          |             | |
3658 AACGAGAAGTCACCACACCTCTCCACTAAAACCCTGAACCTTACTGAGAGAAGCAGAGNCANNAAAGAA 3726
                                          3702           3715
                                                         3714
                                                         3718

3727 CAAATAAAACCCGAAGATGAGACCACCACGTGCGGGACGTTCAGGGGACGGGGAGGAAGAGAATGR 3795
     AvaII                                                              AvaII
     AluI                                                               |
     | |                                                                3863
3796 CGGCGG5MNTTTGGTGGCGGCGGACGTTTTGGTGGCGGGTGGACGTTTTGGTGGCGGCGGTGGA 3864
     3804
     3801         EcoRV     AvaII
                  |         |
3865 CCTTTGGTGGTGGATATCGTGACGAAGGACCTCCCAGTGAAGTCATTGGTTCGTTACTCTTTTCTTAG 3933
                  3880      3892                              DdeI
                                                              |
                                                              3930
```

```
                                                    HindIII
                                                    AluI                          DdeI
      TaqI                                          | |                           | |
      HinfI                                         3976                          4000
      | |                                           3974
3934 TCGAATCTTATTCTGCTCTGCTCGTTGTTTACCGATAAAGCTTAAGACTTTATTGATAAAGTTCTCA 4002
     3935

AluI    XmnI                                           HinfI    DdeI
     | |    | |                                             | |      | |
4003 GCTTTGAATGTGAATGAACTGTTCCTGCTTATTAGTGTTCCTTTGTTTGAGTTGAATCACTGTCTTA 4071
     4004    4023                                           4059     4069
           HinfI
           | |
4072 GCACTTTTGTTAGATTCATCTTTGTGTTAAGTTAAAAGGTAGAAACTTTGTGACTTGTCTCCGTTATG 4140
           4085

HincII
     | |
4141 ACAAGGTTAACTTTGTTGGTTATAACAGAAGTTGCGACCTTTCTCCATGCTTGTGAGGGTGATGCTGTG 4209
     4146

AvaII AluI DdeI     Sau3AI
     | |  | |  | |       | |
4210 GACCAAGCTCTCTCAGGCGAAGATCCCTTACTTCAATGCCCCAATCTACTTGGAAAACAAGACACAGAT 4278
     4217 4222           4231
4210

TaqI
                                         SalI
                                         PstI
                              HindIII    HincII
                     Sau3AI   AluI       AccI EcoRI
                     | |      | |        | | | |   4325
                                         4314 4316 4321
                                         4313
                                         4315
                                         4316
                     4294 4302
                          4300
4279 TGGGAAAGTTGATGAGATCCAAGCTTGGGCTGCAGGTCGACGAATTC 4325
```

FIG. 2J

Brassica campestris ACP Genomic Sequence

```
                                         DdeI
                                         AluI AluI
             AccI                         46  51
             |                            |   |
  1 AAGAGTATGTCTACTACTACTACTCTCTATAATCAAGTTTCAAGAAGCTGAGCTTGGCTCTCACTTTATAT    69
             11                                47

70 GTTTGATGTTGTTGTGCAGGTATGGTAAATCATGGAAAGAGATAAAGAATGCAAACCCTGAAGTATTGG    138

DdeI
             |
139 CAGAGAGGACTGAGGTGAGAGAGCATGTCACTTTTGTGTTACTCATCTGAATTATCTTATATGCGAATT    207
             149

RsaI
             |
208 GTAAGTGGTACTAAAAGGTTTGTAACTTTTGGTAGGTGGATTTGAAGGATAAATGGAGGAACTTGCTTC    276
             217

HindIII                       PvuII
                                      AluI                          AluI
                                      |                             |
277 GGTAGCGGTAACAAGTTTTATATTGCTATGAAGCTTTTTTGCCTGCGTGACGTATCAGCAGCTGTGGAG    345
                                      310                           338
                                      308                           338
```

FIG. 3A

```
                TaqI                    DraI
                HinfI                   —
                —                       715
    691 TGCAATTCGATTCAGTCAATTTAAATTCTTCAAGGTAAATGGGCTGAATACTTGTATAGTTTTAAGAC 759
                699

StuI                                               HindIII
        HaeIII                                             AluI
        BstNI    HaeIII                                    —
        —        —                                         819
        768      778                                       817
    760 TTAACAGGCCTTAAAAGGCCCATGTTATCATAAAAACGTCATTGTTTAGAGTGCACCAAGCTTATATAAAAT 828
        768

StuI
        HaeIII            StuI
        BstNI             HaeIII                           HaeIII
        —                 —                                —
        835               857                              886
    829 GTAGCCAGGCCTTAAAAGACTTAACAGGCCTTAAAAGGCCCATGTTATCA 897
        838               857
        838

AluI           BstNI                  StuI
                                    —                      HaeIII
                                    939                    —
                     927                                   961
    898 TAAAACGTCATCGTTTGAGTGCACCAAGCTAAATGTAGCCAGGCCTTAAAAGACTTAACAGGCCTTAA 966
                                    942                    961
                                    942

FIG. 3C
```

```
                                                                              AluI  AvaI
                                               HindIII                         |    |
                                                AluI                           AGCCAGTACCTC 1035
                                                 |                             1029 1034
967 AAGGCCCATGTTATCATAAAACGCCGTCGTTTGAGTGCACCAAGCTTATAAATGT
    |
    HaeIII
    971                                                                1012
                                                                       1010

XhoI
                                                           TaqI Sau3AI
                                                           AvaI BglII    AvaI      TaqI
                                                            ||   |        |        |
1036 GGGACATCACGCTCTTTGTACACTCCGCCATCTCTCTCTCTCGAGCAGATCTCTCTCGGGAATATCG 1104
                  |                                        1078 1085    1093      1103
                 RsaI                                      1079 1085
                 1055                                      1078

Tth111I
    TaqI
    SalI
    HincII
    AccI
    ||||
1105 ACAAATGTCGACCACTTTCTGCTCTTCCGTCTCCATGCAAGCCACTTCTCTGGTAATCTCCATCTCCTTCT 1173
    |||| METSerThrThrPheCysSerSerValSerMETGlnAlaThrSerLeu
    1112
    1110
    1111
    1112
    1108

Sau3AI
     Sau3AI    BclI                             Sau3AI                Sau3AI
       |       |                                  |                     |
1174 TGTGTTCCAGATCGCTCTGATCATATACTTTCTTTTAGATCATTGCCTCTGATCTGTTGCTTGATGTTT 1242
     1184    1193                              1210                   1224
             1193
```

FIG. 3D

Brassica Campestris Seed Specific cDNA-EA9

```
                        Sau3AI
                        |——|
  1 TTCAACTTTTCTAAACCAAATGCTTTAACACAGATCCAAATCTTTCTCATTGTCTCTCTAGTCTCATC    69
                     METAlaLeuThrGlnIleGlnIlePheLeuIleValSerLeuValSerSe
                                                                         34
    TaqI
    Sau3AI                               TaqI
    ClaI                                 |——|
 70 ATTCAGTTTATCGATCACTCTTTCTCGTCCATTACTCGATGAAGTCGCCATGCAAAAGAGACATGCCGA   138
    rPheSerLeuSerIleThrLeuSerArgProLeuLeuAspLeuLeuAlaAlaMETGlnLysArgHisAlaGl
    81                                                                    106
    82
    81
                              HaeIII
                              |——|
139 GTGGATGACCGAACACGGCCGTGTTTACGCAGATGCGAACAGAGAAAAACAACCGCTACGCTGTTTCAA   207
    uTrpMETThrGluHisGlyArgValTyrAlaAspAlaAsnGluLysAsnAsnArgTyrAlaValPheLy
                                      157
                                           HpaII    DraI
                                           |——|    |——|
208 ACGCAACGTGGAACGCATTGAACGCTTAAATGACGTTCAATCCGGACTAACGTTTAAACTCGCGGTGAA   276
    sArgAsnValGluArgIleGluArgLeuAsnAspValGlnSerGlyLeuThrPheLysLeuAlaValAs
                                      250                          263
```

Complete nucleotide sequence of B. campestris cDNA EA9. The longest open reading frame is designated by three letter amino acid code. PolyA tails are evident at the end of the sequence and a potential polyadenylation signal is underlined.

FIG. 4A

```
                Sau3AI          EcoRI               RsaI
277 CCAGTTTGCTGATCTAACCAACGAAGAATTCCGTTCTATGTACACTGGTTTCAAAGGAAACTCTGTGTT 345
    nGlnPheAlaAspLeuThrAsnGluGluPheArgSerMETTyrThrGlyPheLysGlyAsnSerValIle
              287                          303                 318

TaqI                      RsaI                        HpaII
                                   KpnI
346 GTCTAGTCGAACTAAACCAACGTCGTTTAGGTACCAAAACGTTTCTTCTGATGCGTTGCCGGTTTCTGT 414
    uSerSerArgThrLysProThrSerPheArgTyrGlnAsnValSerSerAspAlaLeuProValSerVa
              353                           378         380        405

AluI               Sau3AI          Sau3AI
415 TGATTGGAGGAAGAAAGGAGCTGTGACTCCTATCAAGGATCAAGGCTTATGCGGATCTTGTTGGGCGTT 483
    lAspTrpArgGlyLysGlyAlaValThrProIleLysAspGlnGlyLeuCysGlySerCysTrpAlaPh
                      435                      452              468

PvuII
                AluI
484 TTCAGCTGTTGCGGCTATAGAAGGAGTAGCACAGATAAAGAAAGGAAACTCATTTCTTGTCTGAACA 552
    eSerAlaValAlaAlaIleGluGlyValAlaGlnIleLysLysGlyLysLeuIleSerLeuSerGluGl
              489
              489
```

FIG. 4B

```
       TaqI
       SalI
       HincII
       AluI AccI
       ┬┬┬  ┬
553  AGAGCTTGTCGACTGCGACACAAACGATGGTGGCTGCATGGGCGGTTTGATGGATACAGCGTTTAACTA   621
     nGluLeuValAspCysAspThrAsnAspGlyGlyCysMETGlyLeuMETAspThrAlaPheAsnTy
                    557 562
                    560
                    561
                    562

622  CACAATAACTATTGGGCGGCTTAACCTCTGAATCAAATTATCCTTATAAAAGCACAAACGGCACTTGCAA   690
     rThrIleThrIleGlyGlyLeuThrSerGluSerAsnTyrProTyrLysSerThrAsnGlyThrCysAs
                                                                HpaII
                                                                ┬─

691  CTTCAATAAACTAAACAGATAGCAACTTCTATCAAAGGTTTTGAGGATGTCCCGGCTAACGATGAGAAA   759
     nPheAsnLysThrLysGlnIleIleAlaThrSerIleLysGlyPheGluAspValProAlaAsnAspGluLy
                                                                   744

760  AGCCCTAATGAAGGCAGTGGCCACACCACCCGGTTAGCCATTGAATAGCGGGAGGAGATATTGGTTTCCA   828
     sAlaLeuMETLysAlaValAlaHisHisProValSerIleGlyIleAlaGlyIleGlyAspIleGlyPheGl
                                         789
                                                                    HpaII
                                                                    ┬─

Sau3AI
                                                             BclI
                                                             ┬─
829  ATTCTATTCGTCCGGTGTCTTCAGCGGAGAATGCACAACTCATCTTGATCACGGGGTAACTGCGGTTGG   897
     nPheTyrSerSerGlyValPheSerGlyValGluCysThrThrHisLeuAspHisGlyValThrAlaValGl
                                                             875
       HpaII                                                 875
       ┬─
                     841
```

FIG. 4C

```
                    ScaI
                    Sau3AI
            RsaI    BamHI    EcoRI      AvaII
   Sau3AI
   HaeIII
898 ATACGGCCGATCTAAAAACGGATTAAAGTACTGGATCCTCAAGAATTCATGGGGACCAAAAATGGGGAGA 966
    yTyrGlyArgSerLysAsnGlyLeuLysTyrTrpIleLeuLysAsnSerTrpGlyLysTrpGlyGl
    904                         931                     941           951
       906                   927
                             927

Sau3AI        EcoRV
967 ACGTGGATACATGAGGATCAAAAAGATATCAAGCCTAAACACGGACAATGTGTCTTGCCATGAATGC 1035
    uArgGlyTyrMETArgIleIleLysLysProLysHisProLysHisGlyGlnCysGlyLeuAlaMETAsnAl
    982                         995

HindIII
              RsaI             HpaII    AluI
1036 TTCGTACCCAACTATGTGAAAAAATCGGTTCAATATCCGGTTAAGCTTTAGAATAAATGTGTGTTGG 1104
     aSerTyrProThrMET
     1041                              1073  1081
                                             1079

1105 TTATATAATTTAAGACTCTGTTGCATGTAATTTGTGAAATGTAAGTTTATGTGATGCAAAAGATTGATA 1173

1174 AAAAAAAAAAAAA 1186
```

FIG. 4D

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 2200 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:1:

```
GTCGAGGCAG  TCACTAACAT  GAAGTTTGAC  GAGGAGCCCA  ACTATGGGAA  GCTTATTTCT      60

CTTTTCGATA  CTCTAATTGA  GCCGTGCGCT  CTATCTAGAC  CAATTAGAAT  TGATGGAGCT     120

CTAAAGGTTG  CTGGCTGTTT  TCTTGTTCAT  ATGATTAACT  TCTAAACTTG  TGTATAAATA     180

TTCTCTGAAA  GTGCTTCTTT  TGGCATATGT  AGGTTGGGCA  AAAACGAGGA  AGATTGCTTC     240

TCAATTTGGA  AGATGATGAA  CAGCCGAAGA  AGAAAATAAG  AATAGGCAGT  CCTGCTACTC     300

AATGGATCTC  AGTCTATAAC  GGTCGTCGTC  CCATGAAACA  GAGGTAACAC  ATTTTTTGCA     360

TATACACTTT  GATAGTTCCT  CACTAACTGT  GTAATCTTTT  GGTAGATATC  ACTACAATGT     420

TGGAGAGACA  ANGCTGCGCN  RRCATATACA  GAAGGGAAAT  GAAGATGGCC  TTTTGATTAG     480

CTGTGTAGCA  TCAGCAGCTA  ATCTCTGGGC  TCTCATCATG  GATGCTGGAA  CTGGATTCAC     540

TTCTCAAGTT  TATGAGTTGT  CACCGGTCTT  CCTACACAAG  GTAATAATCA  GTTGAAGCAA     600

TTAAGAATCA  ATCTGATTTG  TAGTAAACTA  AGAAGAACTT  ACCTTATGAT  TTCCCCGCAG     660

GACTGGATTA  TGGAACAATG  GGAAAAGAAC  TACTATATAA  GCTCCATAGC  GGGTTCAGAT     720

AACGGGAGCT  CTTTAGTTGT  TATGTCAAAA  GGTTAGTGTT  TAGTGAATAA  TAAACTTATT     780

ATCAAAAAGT  CTTCATTGAC  TTATTTATAT  ACTTGTTGTG  AATTGGTAGG  AACTACTTAT     840

TCTCAGCAGT  CATACAAAGT  GAGTGACTCA  TTTCCATTCA  AGTGGATAAA  TAAGAAATGG     900
```

| | | | | | |
|---|---|---|---|---|---|
| AAAGAAGATT | TTCATGTAAC | CTCCATGACA | ACTGCTGGTA | ATCGTTGGGG | TGTGGTAATG | 960 |
| TCGAGGAACT | CTGGCTTCTC | TGATCAGGTA | GGTTTTGTC | TCTTATTGTC | TGGTGTTTTT | 1020 |
| ATTTTCCCCT | GATAGTCTAA | TATGATAAAC | TCTGCGTTGT | GAAAGGTGGT | GGAGCTTGAC | 1080 |
| TTTTTGTACC | CAAGCGATGG | GATACATAGG | AGGTGGGAGA | ATGGGTATAG | AATAACATCA | 1140 |
| ATGGCAGCAA | CTGCGGATCA | AGCAGCTTTC | ATATTAAGCA | TACCAAAGCG | TAAGATGGTG | 1200 |
| GATGAAACTC | AAGAGACTCT | CCGCACCACC | GCCTTTCCAA | GTACTCATGT | CAAGGTTGGT | 1260 |
| TTCTTTAGCT | TTGAACACAG | ATTTGGATCT | TTTTGTTTTG | TTTCCATATA | CATAGGACCT | 1320 |
| GAGAGCTTTT | GGTTGAATTT | TTTTTTTTTC | AGGACAAATG | GGCGAAGAAT | CTGTACATTG | 1380 |
| CATCAATATG | CTATGGCAGG | ACAGTGTGCT | GATGATACAC | ACTTAAGCAT | CATGTGTTGT | 1440 |
| GTTAGAAAGC | CGAAGACAAT | GGAGCGAGC | CTCAGGGTCG | TCATAATACC | AATCAAAGAC | 1500 |
| GTAAAACCAG | ACGCAGTCTC | TTTGGTTGAA | TGTGATGAAA | GGGATGTGTC | TTGGTATGTA | 1560 |
| TGTACGAGTA | ACAAAGAGA | AGATGCAATT | GAGTAGTAGA | AAGATTTGAG | AGCTTTTAA | 1620 |
| AGCCCTTCAA | GTGTGTGCTT | TTATCTTATT | GATATCATCC | ATTTGCGTTG | TTTAATGCGT | 1680 |
| CTTTAGATAT | GTTTCTGTTT | CTTTCTCAGT | GTCTGAATAT | CTGATAAGTG | CAATGTGAGA | 1740 |
| AAGCCACACC | AAACCAAAAT | ATTCAAATCT | TATATTTTA | ATAATGTCGA | ATCACTCGGA | 1800 |
| GTTGCCACCT | TCTGTGCCAA | TTGTGCTGAA | TCTATCACAC | TAAAAAAAC | ATTTCTTCAA | 1860 |
| GGTAATGACT | TGTGGACTAT | GTTCTGAATT | CTCATTAAGT | TTTTATTTTT | TGAAGTTTAA | 1920 |
| GTTTTTACCT | TCTTTTTTGA | AAAATATCGT | TCATAAGATG | TCACGCCAGG | ACATGAGCTA | 1980 |
| CACATCACAT | ATTAGCATGC | AGATGCGGAC | GATTTGTCAC | TCACTTCAAA | CACCTAAAAG | 2040 |
| AGCTTCTCTC | TCACAGCACA | CACACATATG | CATGCAATAT | TTACACGTGA | TCGCCATGCA | 2100 |
| AATCTCCATT | CTCACCTATA | AATTAGAGGC | TCGGCTTCAC | TTTTTACTCA | AACCAAAACT | 2160 |
| CATCACTACA | AAACATACAC | AAATGGCGAA | CAAGCTCTTC | | | 2200 |

( 2 ) INFORMATION FOR SEQ ID NO:2:

( i ) SEQUENCE CHARACTERISTICS:
        ( A ) LENGTH: 4325 base pairs
        ( B ) TYPE: nucleic acid
        ( C ) STRANDEDNESS: both
        ( D ) TOPOLOGY: linear ( i i ) MOLECULE TYPE: DNA (genomic)

( v ) FRAGMENT TYPE: linear ( i x ) FEATURE:
        ( A ) NAME/KEY: CDS
        ( B ) LOCATION: 2152..2703

( x i ) SEQUENCE DESCRIPTION: SEQ ID NO:2:

| | | | | | |
|---|---|---|---|---|---|
| CTCGAGGCAG | TCACTAACAT | GAAGTTTGAC | GAGGAGCCCA | ACTATGGGAA | GCTTATTTCT | 60 |
| CTTTTCGATA | CTCTAATTGA | GCCGTGCGCT | CTATCTAGAC | CAATTAGAAT | TGATGGAGCT | 120 |
| CTAAAGGTTG | CTGGCTGTTT | TCTTGTTCAT | ATGATTAACT | TCTAAACTTG | TGTATAAATA | 180 |
| TTCTCTGAAA | GTGCTTCTTT | TGGCATATGT | AGGTTGGGCA | AAAACGAGGA | AGATTGCTTC | 240 |
| TCAATTTGGA | AGAGGATGAA | CAGCCGAAGA | AGAAAATAAG | AATAGGCAGT | CCTGCTACTC | 300 |
| AATGGATCTC | AGTCTATAAC | GGTCGTCGTC | CCATGAAACA | GAGGTAAAAC | ATTTTTTGCA | 360 |
| TATACACTTT | GAAAGTTCCT | CACTAACTGT | GTAATCTTTT | GGTAGATATC | ACTACAATGT | 420 |
| CGGAGAGACA | ANGGCTGMNC | ANCATATACA | AAAGGGAAAT | GAAGATGGCC | TTTTGATTAG | 480 |
| CTGTGTAGCA | TCAGCAGCTA | ATCTCTGGGC | TCTCATCATG | GATGCTGGAA | CTGGATTCAC | 540 |

```
TTCTCAAGTT TATGAGTTGT CACCGGTCTT CCTACACAAG GTAATAATCA GTTGAAGCAA      600
TTAAGAATCA ATTTGATTTG TAGTAAACTA AGAAGAACTT ACCTTATGTT TTCCCCGCAG      660
GACTGGATTA TGGAACAATG GGAAAAGAAC TACTATATAA GCTCCATAGC TGGTTCAGAT      720
AACGGGAGCT CTTTAGTTGT TATGTCAAAA GGTTAGTGTT TAGTGAATAA TAAACTTATA      780
CCACAAAGTC TTCATTGACT TATTTATATA CTTGTTGTGA ATTGCTAGGA ACTACTTATT      840
CTCAGCAGTC ATACAAAGTG AGTGACTCAT TTCCGTTCAA GTGGATAAAT AAGAAATGGA      900
AAGAAGATTT TCATGTAACC TCCATGACAA CTGCTGGTAA TCGTTGGGGT GTGGTAATGT      960
CGAGGAACTC TGGCTTCTCT GATCAGGTAG GTTTTGTCT CTTATTGTCT GGTGTTTTA      1020
TTTTCCCCTG ATAGTCTAAT ATGATAAACT CTGCGTTGTG AAAGGTGGTG GAGCTTGACT     1080
TTTTGTACCC AAGCGATGGG ATACATAGGA GGTGGGAGAA TGGGTATAGA ATAACATCAA     1140
TGGCAGCAAC TGCGGATCAA GCAGCTTTCA TATTAAGCAT ACCAAAGCGT AAGATGGTGG     1200
ATGAAACTCA AGAGACTCTC CGCACCACCG CCTTTCCAAG TACTCATGTC AAGGTTGGTT     1260
TCTTTAGCTT TGAACACAGA TTTGGATCTT TTTGTTTTGT TTCCATATAC TTAGGACCTG     1320
AGAGCTTTTG GTTGATTTTT TTTTCAGGAC AAATGGGCGA AGAATCTGTA CATTGCATCA     1380
ATATGCTATG GCAGGACAGT GTGCTGATAC ACACTTAAGC ATCATGTGGA AAGCCAAAGA     1440
CAATTGGAGC GAGACTCAGG GTCGTCATAA TACCAATCAA AGACGTAAAA CCAGACGCAA     1500
CCTCTTTGGT TGAATGTAAT GAAAGGGATG TGTCTTGGTA TGTATGTACG AATAACAAAA     1560
GAGAAGATGG AATTAGTAGT AGAAATATTT GGGAGCTTTT TAAGCCCTTC AAGTGTGCTT     1620
TTTATCTTAT TGATATCATC CATTTGCGTT GTTAATGCG TCTCTAGATA TGTTCCTATA     1680
TCTTTCTCAG TGTCTGATAA GTGAAATGTG AGAAAACCAT ACCAAACCAA AATATTCAAA     1740
TCTTATTTTT AATAATGTTG AATCACTCGG AGTTGCCACC TTCTGTGCCA ATTGTGCTGA     1800
ATCTATCACA CTAGAAAAAA ACATTCTTC AAGGTAATGA CTTGTGGACT ATGTTCTGAA     1860
TTCTCATTAA GTTTTTATTT TCTGAAGTTT AAGTTTTTAC CTTCTGTTTT GAAATATATC     1920
GTTCATAAGA TGTCACGCCA GGACATGAGC TACACATCGC ACATAGCATG CAGATCAGGA     1980
CGATTGTCA CTCACTTCAA ACACCTAAGA GCTTCTCTCT CACAGCGCAC ACACATATGC     2040
ATGCAATATT TACACGTGAT CGCCATGCAA ATCTCCATTC TCACCTATAA ATTAGAGCCT     2100
CGGCTTCACT CTTTACTCAA ACCAAAACTC ATCACTACAG AACATACACA A ATG GCG     2157
                                                          Met Ala
                                                           1

AAC AAG CTC TTC CTC GTC TCG GCA ACT CTC GCC TTG TTC TTC CTT CTC       2205
Asn Lys Leu Phe Leu Val Ser Ala Thr Leu Ala Leu Phe Phe Leu Leu
         5                  10                  15

ACC AAT GCC TCC GTC TAC AGG ACG GTT GTG GAA GTC GAC GAA GAT GAT       2253
Thr Asn Ala Ser Val Tyr Arg Thr Val Val Glu Val Asp Glu Asp Asp
         20                  25                  30

GCC ACA AAT CCA GCC GGC CCA TTT AGG ATT CCA AAA TGT AGG AAG GAG       2301
Ala Thr Asn Pro Ala Gly Pro Phe Arg Ile Pro Lys Cys Arg Lys Glu
 35                  40                  45                  50

TTT CAG CAA GCA CAA CAC CTG AAA GCT TGC CAA CAA TGG CTC CAC AAG       2349
Phe Gln Gln Ala Gln His Leu Lys Ala Cys Gln Gln Trp Leu His Lys
             55                  60                  65

CAG GCA ATG CAG TCC GGT AGT GGT CCA AGC TGG ACC CTC GAT GGT GAG       2397
Gln Ala Met Gln Ser Gly Ser Gly Pro Ser Trp Thr Leu Asp Gly Glu
         70                  75                  80

TTT GAT TTT GAA GAC GAC GTG GAG AAC CAA CAA CAG GGC CCG CAG CAG       2445
Phe Asp Phe Glu Asp Asp Val Glu Asn Gln Gln Gln Gly Pro Gln Gln
         85                  90                  95
```

| | | | | | | | | | | | | | | | | |
|---|---|---|---|---|---|---|---|---|---|---|---|---|---|---|---|---|
| AGG | CCA | CCG | CTG | CTC | CAG | CAG | TGC | TGC | AAC | GAG | CTC | CAC | CAG | GAA | GAG | 2493 |
| Arg | Pro | Pro | Leu | Leu | Gln | Gln | Cys | Cys | Asn | Glu | Leu | His | Gln | Glu | Glu | |
| | 100 | | | | 105 | | | | | 110 | | | | | | |
| CCA | CTT | TGC | GTT | TGC | CCA | ACC | TTG | AAA | GGA | GCA | TCC | AAA | GCC | GTT | AAA | 2541 |
| Pro | Leu | Cys | Val | Cys | Pro | Thr | Leu | Lys | Gly | Ala | Ser | Lys | Ala | Val | Lys | |
| 115 | | | | | 120 | | | | | 125 | | | | | 130 | |
| CAA | CAG | ATT | CGA | CAA | CAA | CAG | GGA | CAA | CAA | ATG | CAG | GGA | CAG | CAG | ATG | 2589 |
| Gln | Gln | Ile | Arg | Gln | Gln | Gln | Gly | Gln | Gln | Met | Gln | Gly | Gln | Gln | Met | |
| | | | | 135 | | | | | 140 | | | | | 145 | | |
| CAG | CAA | GTG | ATT | AGC | CGT | ATC | TAC | CAG | ACC | GCT | ACG | CAC | TTA | CCT | AGA | 2637 |
| Gln | Gln | Val | Ile | Ser | Arg | Ile | Tyr | Gln | Thr | Ala | Thr | His | Leu | Pro | Arg | |
| | | | 150 | | | | | 155 | | | | | 160 | | | |
| GCT | TGC | AAC | ATC | AGG | CAA | GTT | AGC | ATT | TGC | CCC | TTC | CAG | AAG | ACC | ATG | 2685 |
| Ala | Cys | Asn | Ile | Arg | Gln | Val | Ser | Ile | Cys | Pro | Phe | Gln | Lys | Thr | Met | |
| | | 165 | | | | | 170 | | | | | 175 | | | | |
| CCT | GGG | CCC | GGC | TTC | TAC | TAGATTCCAA | ACGAATATCC | TCGAGAGTGT | | | | | | | | 2733 |
| Pro | Gly | Pro | Gly | Phe | Tyr | | | | | | | | | | | |
| | 180 | | | | | | | | | | | | | | | |

```
GTATACCACG GTGATATGAG TGTGGTTGTT GATGTATGTT AACACTACAT AGTCATGGTG    2793
TGTGTTCCAT AAATAATGTA CTAATGTAAT AAGAACTACT CCGTAGACGG TAATAAAAGA    2853
GAAGTTTTTT TTTTTACTCT TGCTACTTTC CTATAAAGTG ATGATTAACA ACAGATACAC    2913
CAAAAGAAA  ACAATTAATC TATATTCACA ATGAAGCAGT ACTAGTCTAT TGAACATGTC    2973
AGATTTCTT  TTTCTAAATG TCTAATTAAG CCTTCAAGGC TAGTGATGAT AAAAGATCAT    3033
CCAATGGGAT CCAACAAAGA CTCAAATCTG GTTTGATCA  GATACTTCAA AACTATTTTT    3093
GTATTCATTA AATTATGCAA GTGTTCTTTT ATTGGTGAA  GACTCTTTAG AAGCAAAGAA    3153
CGACAAGCAG TAATAAAAAA AACAAAGTTC AGTTTTAAGA TTTGTTATTG ACTTATTGTC    3213
ATTTGAAAAA TATAGTATGA TATTAATATA GTTTTATTTA TATAATGCTT GTCTATTCAA    3273
GATTTGAGAA CATTAATATG ATACTGTCCA CATATCCAAT ATATTAAGTT TCATTTCTGT    3333
TCAAACATAT GATAAGATGG TCAAATGATT ATGAGTTTTG TTATTTACCT GAAGAAAAGA    3393
TAAGTGAGCT TCGAGTTTCT GAAGGGTACG TGATCTTCAT TTCTTGGCTA AAAGCGAATA    3453
TGACATCACC TAGAGAAAGC CGATAATAGT AAACTCTGTT CTTGGTTTTT GGTTTAATCA    3513
AACCGAACCG GTAGCTGAGT GTCAAGTCAG CAAACATCGC AAACCATATG TCAATTCGTT    3573
AGATTCCCGG TTTAAGTTGT AAACCGGTAT TTCATTTGGT GAAAACCCTA GAAGCCAGCC    3633
ANCCTTTTTA ATCTAATTTT TGCAAACGAG AAGTCACCAC ACCTCTCCAC TAAAACCCTG    3693
AACCTTACTG AGAGAAGCAG AGNCANNAAA GAACAAATAA AACCCGAAGA TGAGACCACC    3753
ACGTGCGGCG GGACGTTCAG GGGACGGGGA GGAAGAGAAT GRCGGCGGNM NTTTGGTGGC    3813
GGCGGCGGAC GTTTTGGTGG CGGCGGTGGA CGTTTTGGTG GCGGCGGTGG ACCTTTGGTG    3873
GTGGATATCG TGACGAAGGA CCTCCCAGTG AAGTCATTGG TTCGTTTACT CTTTTCTTAG    3933
TCGAATCTTA TTCTTGCTCT GCTCGTTGTT TTACCGATAA AGCTTAAGAC TTTATTGATA    3993
AAGTTCTCAG CTTTGAATGT GAATGAACTG TTTCCTGCTT ATTAGTGTTC CTTTGTTTTG    4053
AGTTGAATCA CTGTCTTAGC ACTTTTGTTA GATTCATCTT TGTGTTTAAG TTAAAGGTA     4113
GAAACTTTGT GACTTGTCTC CGTTATGACA AGGTTAACTT TGTTGGTTAT AACAGAAGTT    4173
GCGACCTTTC TCCATGCTTG TGAGGGTGAT GCTGTGGACC AAGCTCTCTC AGGCGAAGAT    4233
CCCTTACTTC AATGCCCCAA TCTACTTGGA AAACAAGACA CAGATTGGGA AAGTTGATGA    4293
GATCCAAGCT TGGGCTGCAG GTCGACGAAT TC                                  4325
```

(2) INFORMATION FOR SEQ ID NO:3:

(i) SEQUENCE CHARACTERISTICS:
        (A) LENGTH: 184 amino acids
        (B) TYPE: amino acid
        (D) TOPOLOGY: linear (ii) MOLECULE TYPE: protein (xi) SEQUENCE DESCRIPTION: SEQ ID NO:3:

```
Met Ala Asn Lys Leu Phe Leu Val Ser Ala Thr Leu Ala Leu Phe Phe
 1               5                  10                  15

Leu Leu Thr Asn Ala Ser Val Tyr Arg Thr Val Val Glu Val Asp Glu
            20                  25                  30

Asp Asp Ala Thr Asn Pro Ala Gly Pro Phe Arg Ile Pro Lys Cys Arg
        35                  40                  45

Lys Glu Phe Gln Gln Ala Gln His Leu Lys Ala Cys Gln Gln Trp Leu
    50                  55                  60

His Lys Gln Ala Met Gln Ser Gly Ser Gly Pro Ser Trp Thr Leu Asp
65                  70                  75                  80

Gly Glu Phe Asp Phe Glu Asp Asp Val Glu Asn Gln Gln Gln Gly Pro
                85                  90                  95

Gln Gln Arg Pro Pro Leu Leu Gln Gln Cys Cys Asn Glu Leu His Gln
            100                 105                 110

Glu Glu Pro Leu Cys Val Cys Pro Thr Leu Lys Gly Ala Ser Lys Ala
        115                 120                 125

Val Lys Gln Gln Ile Arg Gln Gln Gln Gly Gln Gln Met Gln Gly Gln
    130                 135                 140

Gln Met Gln Gln Val Ile Ser Arg Ile Tyr Gln Thr Ala Thr His Leu
145                 150                 155                 160

Pro Arg Ala Cys Asn Ile Arg Gln Val Ser Ile Cys Pro Phe Gln Lys
                165                 170                 175

Thr Met Pro Gly Pro Gly Phe Tyr
            180
```

(2) INFORMATION FOR SEQ ID NO:4:

(i) SEQUENCE CHARACTERISTICS:
        (A) LENGTH: 2154 base pairs
        (B) TYPE: nucleic acid
        (C) STRANDEDNESS: both
        (D) TOPOLOGY: linear (ii) MOLECULE TYPE: DNA (genomic)

(ix) FEATURE:
        (A) NAME/KEY: CDS
        (B) LOCATION: 1108..1155

(ix) FEATURE:
        (A) NAME/KEY: CDS
        (B) LOCATION: 1462..1569

(ix) FEATURE:
        (A) NAME/KEY: CDS
        (B) LOCATION: 1647..1769

(ix) FEATURE:
        (A) NAME/KEY: CDS
        (B) LOCATION: 1855..1977

(xi) SEQUENCE DESCRIPTION: SEQ ID NO:4:

```
AAGAGTATGT CTACTACTAC TACTCTATAA TCAAGTTTCA AGAAGCTGAG CTTGGCTCTC    60
ACTTTATATG TTTGATGTTG TTGTGCAGGT ATGGTAAATC ATGGAAAGAG ATAAAGAATG   120
```

| | |
|---|---|
| CAAACCCTGA AGTATTGGCA GAGAGGACTG AGGTGAGAGA GCATGTCACT TTTGTGTTAC | 180 |
| TCATCTGAAT TATCTTATAT GCGAATTGTA AGTGGTACTA AAAGGTTTGT AACTTTTGGT | 240 |
| AGGTGGATTT GAAGGATAAA TGGAGGAACT TGCTTCGGTA GCGGTAACAA GTTTTATATT | 300 |
| GCTATGAAGC TTTTTTGCCT GCGTGACGTA TCAGCAGCTG TGGAGAAGAT GGTATTAGAA | 360 |
| AGGGTCTTTT CACATTTGT GTTGTGACAA ATATTAATTC GGCCGGTATG GTTTGGTTAA | 420 |
| GACTTGTTGA GAGACGTGTG GGGTTTTTG ATGTATAATT AGTCTGTGTT TAGAACGAAA | 480 |
| CAAGACTTGT TGNGTATGCT TTTTTTAACT TGAGGGGGTT TGTTGTTGTT AGTTAGGAAC | 540 |
| TTGACTTTGT CTCTTTCTCT CAAGATCTGA TTGGTAAGGT CTGGGTGGTA GTACTGTTTG | 600 |
| GTTTAATTTG TTTTGACTAT TGAGTCACTG TGGCCCATTG ACTTTAAATT AGGCTGGTAT | 660 |
| ATTTTTTGGT TTAAAACCGG TCTGAGATAG TGCAATTTCG ATTCAGTCAA TTTTAAATTC | 720 |
| TTCAAGGTAA TGGGCTGAAT ACTTGTATAG TTTTAAGACT TAACAGGCCT TAAAAGGCCC | 780 |
| ATGTTATCAT AAAACGTCAT TGTTTAGAGT GCACCAAGCT TATAAAATGT AGCCAGGCCT | 840 |
| TAAAAGACTT AACAGGCCTT AAAAGACTTA ACATTCCTTA AAAGGCCCAT GTTATCATAA | 900 |
| AACGTCATCG TTTTGAGTGC ACCAAGCTAA ATGTAGCCAG GCCTTAAAAG ACTTAACAGG | 960 |
| CCTTAAAAGG CCCATGTTAT CATAAAACGC CGTCGTTTTG AGTGCACCAA GCTTATAAAT | 1020 |
| GTAGCCAGCT ACCTCGGGAC ATCACGCTCT TTGTACACTC CGCCATCTCT CTCTCTCTCG | 1080 |
| AGCAGATCTC TCTCGGGAAT ATCGACA ATG TCG ACC ACT TTC TGC TCT TCC | 1131 |
|                              Met Ser Thr Thr Phe Cys Ser Ser | |
|                               1                       5     | |
| GTC TCC ATG CAA GCC ACT TCT CTG GTAATCTCAT CTCCTTCTTG TGTTCCCAGA | 1185 |
| Val Ser Met Gln Ala Thr Ser Leu | |
|      10              15        | |
| TCGCTCTGAT CATACTTTCT TTAGATCAT TTGCCTCTGA TCTGTTGCTT GATGTTTGTT | 1245 |
| AACTCTCCAC GCATGTTTGA TTATGTTGAG AATTAGAAAA AAAATGTTAG CTTTACGAAT | 1305 |
| CTTTAGTGAT CATTTCAATT GGATTTGCAA TCTTGTGTGA CATTTGAGGC TTGTGTAGAT | 1365 |
| TTCGATCTGT ATTCATTTTG AATCACAGCT ATAATAGTCA TTTGAGTAGT AGTGTTTTA | 1425 |
| AATGAACATG TTTTGTTGTA TTGATGGAAC AAACAG GCA GCA ACA ACG AGG ATT | 1479 |
|                                        Ala Ala Thr Thr Arg Ile | |
|                                         1                   5  | |
| AGT TTC CAG AAG CCA GCT TTG GTT TCA ACG ACT AAT CTC TCC TTC AAC | 1527 |
| Ser Phe Gln Lys Pro Ala Leu Val Ser Thr Thr Asn Leu Ser Phe Asn | |
|              10              15              20                | |
| CTC CGC CGT TCA ATC CCC ACT CGT TTC TCA ATC TCC TGC GCG | 1569 |
| Leu Arg Arg Ser Ile Pro Thr Arg Phe Ser Ile Ser Cys Ala | |
|      25              30              35                | |
| GTATGTTCTC ATTCTCAGCA TTTATTTCGA GCTTGCTTGT CATGGTACTC TCTCTAATTG | 1629 |
| TCTATTTGGT TTATTAG GCC AAA CCA GAG ACG GTT GAG AAA GTG TCT AAG | 1679 |
|              Ala Lys Pro Glu Thr Val Glu Lys Val Ser Lys | |
|               1               5                      10  | |
| ATA GTT AAG AAG CAG CTA TCA CTC AAA GAC GAC CAA AAG GTC GTT GCG | 1727 |
| Ile Val Lys Lys Gln Leu Ser Leu Lys Asp Asp Gln Lys Val Val Ala | |
|              15              20              25                | |
| GAG ACC AAG TTT GCT GAT CTT GGA GCA GAT TCT CTC GAC ACT | 1769 |
| Glu Thr Lys Phe Ala Asp Leu Gly Ala Asp Ser Leu Asp Thr | |
|      30              35              40                | |
| GTAAGTCATC AATCATTCTC TTATGTGAAT AAAGAGAACT TGAAGAGTTT GTTTTTAACA | 1829 |
| TATTAACTGA GTGTTTTGCA TGCAG GTT GAG ATA GTG ATG GGT TTA GAG GAA | 1881 |
|                            Val Glu Ile Val Met Gly Leu Glu Glu | |
|                             1                       5          | |

```
GAG  TTT  GAT  ATC  GAA  ATG  GCT  GAA  GAG  AAA  GCT  CAG  AAG  ATT  GCT  ACT    1929
Glu  Phe  Asp  Ile  Glu  Met  Ala  Glu  Glu  Lys  Ala  Gln  Lys  Ile  Ala  Thr
 10                       15                       20                       25

GTG  GAG  GAA  GCT  GCT  GAA  CTC  ATT  GAA  GAG  CTC  GTT  CAA  CTT  AAG  AAG    1977
Val  Glu  Glu  Ala  Ala  Glu  Leu  Ile  Glu  Glu  Leu  Val  Gln  Leu  Lys  Lys
                    30                       35                       40

TAATTTTAGT  ATTAAGAGCA  GCCAAGGCTT  TGTTGGGTTT  GTTGTTTTCA  TAATCTTCCT           2037

GTCATTTTCT  TTTTCTTTAA  TGTGTCAAGC  GACTCTGTTG  GTTTAAAGTA  GTATCTGTTT           2097

GCCATGGATC  TCTCTCTATT  TGTCGACTGA  AAACTTTTGG  TTTACACATG  AAAGCTT             2154
```

( 2 ) INFORMATION FOR SEQ ID NO:5:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: protein ( x i ) SEQUENCE DESCRIPTION: SEQ ID NO:5:

```
Met  Ser  Thr  Thr  Phe  Cys  Ser  Ser  Val  Ser  Met  Gln  Ala  Thr  Ser  Leu
 1                   5                        10                       15
```

( 2 ) INFORMATION FOR SEQ ID NO:6:

( i ) SEQUENCE CHARACTERISTICS:
    ( A ) LENGTH: 36 amino acids
    ( B ) TYPE: amino acid
    ( D ) TOPOLOGY: linear ( i i ) MOLECULE TYPE: protein ( x i ) SEQUENCE DESCRIPTION: SEQ ID NO:6:

```
Ala  Ala  Thr  Thr  Arg  Ile  Ser  Phe  Gln  Lys  Pro  Ala  Leu  Val  Ser  Thr
 1                   5                        10                       15

Thr  Asn  Leu  Ser  Phe  Asn  Leu  Arg  Arg  Ser  Ile  Pro  Thr  Arg  Phe  Ser
               20                       25                       30

Ile  Ser  Cys  Ala
          35
```

( 2 ) INFORMATION FOR SEQ ID NO:7:

( i ) SEQUENCE CHARACTERISTICS:
    ( A ) LENGTH: 41 amino acids
    ( B ) TYPE: amino acid
    ( D ) TOPOLOGY: linear ( i i ) MOLECULE TYPE: protein ( x i ) SEQUENCE DESCRIPTION: SEQ ID NO:7:

```
Ala  Lys  Pro  Glu  Thr  Val  Glu  Lys  Val  Ser  Lys  Ile  Val  Lys  Lys  Gln
 1                   5                        10                       15

Leu  Ser  Leu  Lys  Asp  Asp  Gln  Lys  Val  Val  Ala  Glu  Thr  Lys  Phe  Ala
               20                       25                       30

Asp  Leu  Gly  Ala  Asp  Ser  Leu  Asp  Thr
          35                       40
```

( 2 ) INFORMATION FOR SEQ ID NO:8:

( i ) SEQUENCE CHARACTERISTICS:
    ( A ) LENGTH: 41 amino acids
    ( B ) TYPE: amino acid
    ( D ) TOPOLOGY: linear ( i i ) MOLECULE TYPE: protein ( x i ) SEQUENCE DESCRIPTION: SEQ ID NO:8:

```
Val  Glu  Ile  Val  Met  Gly  Leu  Glu  Glu  Glu  Phe  Asp  Ile  Glu  Met  Ala
 1              5                        10                       15

Glu  Glu  Lys  Ala  Gln  Lys  Ile  Ala  Thr  Val  Glu  Glu  Ala  Ala  Glu  Leu
              20                        25                       30

Ile  Glu  Glu  Leu  Val  Gln  Leu  Lys  Lys
         35                       40
```

( 2 ) INFORMATION FOR SEQ ID NO:9:

( i ) SEQUENCE CHARACTERISTICS:
        ( A ) LENGTH: 1186 base pairs
        ( B ) TYPE: nucleic acid
        ( C ) STRANDEDNESS: both
        ( D ) TOPOLOGY: linear ( i i ) MOLECULE TYPE: DNA (genomic)

( i x ) FEATURE:
        ( A ) NAME/KEY: CDS
        ( B ) LOCATION: 20..1051

( x i ) SEQUENCE DESCRIPTION: SEQ ID NO:9:

```
TTCAACTTTT  CTAAACCAA  ATG  GCT  TTA  ACA  CAG  ATC  CAA  ATC  TTT  CTC  ATT       52
                       Met  Ala  Leu  Thr  Gln  Ile  Gln  Ile  Phe  Leu  Ile
                        40                             45

GTC  TCT  CTA  GTC  TCA  TCA  TTC  AGT  TTA  TCG  ATC  ACT  CTT  TCT  CGT  CCA    100
Val  Ser  Leu  Val  Ser  Ser  Phe  Ser  Leu  Ser  Ile  Thr  Leu  Ser  Arg  Pro
 50                       55                            60                  65

TTA  CTC  GAT  GAA  GTC  GCC  ATG  CAA  AAG  AGA  CAT  GCC  GAG  TGG  ATG  ACC    148
Leu  Leu  Asp  Glu  Val  Ala  Met  Gln  Lys  Arg  His  Ala  Glu  Trp  Met  Thr
                    70                       75                      80

GAA  CAC  GGC  CGT  GTT  TAC  GCA  GAT  GCG  AAC  GAG  AAA  AAC  AAC  CGC  TAC    196
Glu  His  Gly  Arg  Val  Tyr  Ala  Asp  Ala  Asn  Glu  Lys  Asn  Asn  Arg  Tyr
               85                            90                      95

GCT  GTT  TTC  AAA  CGC  AAC  GTG  GAA  CGC  ATT  GAA  CGC  TTA  AAT  GAC  GTT    244
Ala  Val  Phe  Lys  Arg  Asn  Val  Glu  Arg  Ile  Glu  Arg  Leu  Asn  Asp  Val
              100                           105                     110

CAA  TCC  GGA  CTA  ACG  TTT  AAA  CTC  GCG  GTG  AAC  CAG  TTT  GCT  GAT  CTA    292
Gln  Ser  Gly  Leu  Thr  Phe  Lys  Leu  Ala  Val  Asn  Gln  Phe  Ala  Asp  Leu
115                           120                      125

ACC  AAC  GAA  GAA  TTC  CGT  TCT  ATG  TAC  ACT  GGT  TTC  AAA  GGA  AAC  TCT    340
Thr  Asn  Glu  Glu  Phe  Arg  Ser  Met  Tyr  Thr  Gly  Phe  Lys  Gly  Asn  Ser
130                           135                      140                145

GTG  TTG  TCT  AGT  CGA  ACT  AAA  CCA  ACG  TCG  TTT  AGG  TAC  CAA  AAC  GTT    388
Val  Leu  Ser  Ser  Arg  Thr  Lys  Pro  Thr  Ser  Phe  Arg  Tyr  Gln  Asn  Val
                    150                      155                     160

TCT  TCT  GAT  GCG  TTG  CCG  GTT  TCT  GTT  GAT  TGG  AGG  AAG  AAA  GGA  GCT    436
Ser  Ser  Asp  Ala  Leu  Pro  Val  Ser  Val  Asp  Trp  Arg  Lys  Lys  Gly  Ala
               165                           170                     175

GTG  ACT  CCT  ATC  AAG  GAT  CAA  GGC  TTA  TGC  GGA  TCT  TGT  TGG  GCG  TTT    484
Val  Thr  Pro  Ile  Lys  Asp  Gln  Gly  Leu  Cys  Gly  Ser  Cys  Trp  Ala  Phe
              180                            185                     190

TCA  GCT  GTT  GCG  GCT  ATA  GAA  GGA  GTA  GCA  CAG  ATA  AAG  AAA  GGG  AAA    532
Ser  Ala  Val  Ala  Ala  Ile  Glu  Gly  Val  Ala  Gln  Ile  Lys  Lys  Gly  Lys
         195                            200                      205

CTC  ATT  TCT  TTG  TCT  GAA  CAA  GAG  CTT  GTC  GAC  TGC  GAC  ACA  AAC  GAT    580
Leu  Ile  Ser  Leu  Ser  Glu  Gln  Glu  Leu  Val  Asp  Cys  Asp  Thr  Asn  Asp
210                           215                      220                225

GGT  GGC  TGC  ATG  GGC  GGT  TTG  ATG  GAT  ACA  GCG  TTT  AAC  TAC  ACA  ATA    628
Gly  Gly  Cys  Met  Gly  Gly  Leu  Met  Asp  Thr  Ala  Phe  Asn  Tyr  Thr  Ile
                    230                      235                     240
```

| | | | | | | | | | | | | | | | | |
|---|---|---|---|---|---|---|---|---|---|---|---|---|---|---|---|---|
| ACT | ATT | GGC | GGC | TTA | ACC | TCT | GAA | TCA | AAT | TAT | CCT | TAT | AAA | AGC | ACA | 676 |
| Thr | Ile | Gly | Gly | Leu | Thr | Ser | Glu | Ser | Asn | Tyr | Pro | Tyr | Lys | Ser | Thr | |
| | | 245 | | | | | 250 | | | | | | 255 | | | |
| AAC | GGC | ACT | TGC | AAC | TTC | AAT | AAA | ACT | AAA | CAG | ATA | GCA | ACT | TCT | ATC | 724 |
| Asn | Gly | Thr | Cys | Asn | Phe | Asn | Lys | Thr | Lys | Gln | Ile | Ala | Thr | Ser | Ile | |
| | | 260 | | | | | 265 | | | | | 270 | | | | |
| AAA | GGT | TTT | GAG | GAT | GTC | CCG | GCT | AAC | GAT | GAG | AAA | GCC | CTA | ATG | AAG | 772 |
| Lys | Gly | Phe | Glu | Asp | Val | Pro | Ala | Asn | Asp | Glu | Lys | Ala | Leu | Met | Lys | |
| | 275 | | | | | 280 | | | | | 285 | | | | | |
| GCA | GTG | GCA | CAC | CAC | CCG | GTT | AGC | ATT | GGA | ATA | GCG | GGA | GGA | GAT | ATT | 820 |
| Ala | Val | Ala | His | His | Pro | Val | Ser | Ile | Gly | Ile | Ala | Gly | Gly | Asp | Ile | |
| 290 | | | | | 295 | | | | 300 | | | | | | 305 | |
| GGT | TTC | CAA | TTC | TAT | TCG | TCC | GGT | GTG | TTC | AGC | GGA | GAA | TGC | ACA | ACT | 868 |
| Gly | Phe | Gln | Phe | Tyr | Ser | Ser | Gly | Val | Phe | Ser | Gly | Glu | Cys | Thr | Thr | |
| | | | | 310 | | | | | 315 | | | | | 320 | | |
| CAT | CTT | GAT | CAC | GGG | GTA | ACT | GCG | GTT | GGA | TAC | GGC | CGA | TCT | AAA | AAC | 916 |
| His | Leu | Asp | His | Gly | Val | Thr | Ala | Val | Gly | Tyr | Gly | Arg | Ser | Lys | Asn | |
| | | | 325 | | | | | 330 | | | | | 335 | | | |
| GGA | TTA | AAG | TAC | TGG | ATC | CTC | AAG | AAT | TCA | TGG | GGA | CCA | AAA | TGG | GGA | 964 |
| Gly | Leu | Lys | Tyr | Trp | Ile | Leu | Lys | Asn | Ser | Trp | Gly | Pro | Lys | Trp | Gly | |
| | | 340 | | | | | 345 | | | | | 350 | | | | |
| GAA | CGT | GGA | TAC | ATG | AGG | ATC | AAA | AAA | GAT | ATC | AAG | CCT | AAA | CAC | GGA | 1012 |
| Glu | Arg | Gly | Tyr | Met | Arg | Ile | Lys | Lys | Asp | Ile | Lys | Pro | Lys | His | Gly | |
| | 355 | | | | | 360 | | | | | 365 | | | | | |
| CAA | TGT | GGT | CTT | GCC | ATG | AAT | GCT | TCG | TAC | CCA | ACT | ATG | TGAAAAAATC | | | 1061 |
| Gln | Cys | Gly | Leu | Ala | Met | Asn | Ala | Ser | Tyr | Pro | Thr | Met | | | | |
| 370 | | | | | 375 | | | | | 380 | | | | | | |

GGTTCAATAT CCGGTTAAGC TTTAGAATAA ATGTGTGTGT TGGTTATAAT TTAAGACTCT    1121

GTTGCATGTA ATTTGTGAAA TGGTAAGTTT ATGTGATGCA AAGATTTGA TAAAAAAAAA    1181

AAAAA    1186

( 2 ) INFORMATION FOR SEQ ID NO:10:

( i ) SEQUENCE CHARACTERISTICS:
        ( A ) LENGTH: 344 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| | | | | | | | | | | | | | | |
|---|---|---|---|---|---|---|---|---|---|---|---|---|---|---|
| Met | Ala | Leu | Thr | Gln | Ile | Gln | Ile | Phe | Leu | Ile | Val | Ser | Leu | Val | Ser |
| 1 | | | | 5 | | | | | 10 | | | | | 15 | |
| Ser | Phe | Ser | Leu | Ser | Ile | Thr | Leu | Ser | Arg | Pro | Leu | Leu | Asp | Glu | Val |
| | | | 20 | | | | | 25 | | | | | 30 | | |
| Ala | Met | Gln | Lys | Arg | His | Ala | Glu | Trp | Met | Thr | Glu | His | Gly | Arg | Val |
| | | 35 | | | | | 40 | | | | | 45 | | | |
| Tyr | Ala | Asp | Ala | Asn | Glu | Lys | Asn | Asn | Arg | Tyr | Ala | Val | Phe | Lys | Arg |
| | 50 | | | | | 55 | | | | | 60 | | | | |
| Asn | Val | Glu | Arg | Ile | Glu | Arg | Leu | Asn | Asp | Val | Gln | Ser | Gly | Leu | Thr |
| 65 | | | | | 70 | | | | | 75 | | | | | 80 |
| Phe | Lys | Leu | Ala | Val | Asn | Gln | Phe | Ala | Asp | Leu | Thr | Asn | Glu | Glu | Phe |
| | | | | 85 | | | | | 90 | | | | | 95 | |
| Arg | Ser | Met | Tyr | Thr | Gly | Phe | Lys | Gly | Asn | Ser | Val | Leu | Ser | Ser | Arg |
| | | | 100 | | | | | 105 | | | | | 110 | | |
| Thr | Lys | Pro | Thr | Ser | Phe | Arg | Tyr | Gln | Asn | Val | Ser | Ser | Asp | Ala | Leu |
| | | 115 | | | | | 120 | | | | | 125 | | | |
| Pro | Val | Ser | Val | Asp | Trp | Arg | Lys | Lys | Gly | Ala | Val | Thr | Pro | Ile | Lys |

|     |     |     |     |     |     |     |     |     |     |     |     |     |     |     |     |
|-----|-----|-----|-----|-----|-----|-----|-----|-----|-----|-----|-----|-----|-----|-----|-----|
|     |     |     |     | 130 |     |     |     | 135 |     |     |     | 140 |     |     |     |
| Asp | Gln | Gly | Leu | Cys | Gly | Ser | Cys | Trp | Ala | Phe | Ser | Ala | Val | Ala | Ala |
| 145 |     |     |     | 150 |     |     |     | 155 |     |     |     |     |     |     | 160 |
| Ile | Glu | Gly | Val | Ala | Gln | Ile | Lys | Lys | Gly | Lys | Leu | Ile | Ser | Leu | Ser |
|     |     |     |     | 165 |     |     |     | 170 |     |     |     |     |     | 175 |     |
| Glu | Gln | Glu | Leu | Val | Asp | Cys | Asp | Thr | Asn | Asp | Gly | Gly | Cys | Met | Gly |
|     |     |     | 180 |     |     |     |     | 185 |     |     |     |     | 190 |     |     |
| Gly | Leu | Met | Asp | Thr | Ala | Phe | Asn | Tyr | Thr | Ile | Thr | Ile | Gly | Gly | Leu |
|     |     | 195 |     |     |     |     | 200 |     |     |     |     | 205 |     |     |     |
| Thr | Ser | Glu | Ser | Asn | Tyr | Pro | Tyr | Lys | Ser | Thr | Asn | Gly | Thr | Cys | Asn |
|     | 210 |     |     |     |     | 215 |     |     |     |     | 220 |     |     |     |     |
| Phe | Asn | Lys | Thr | Lys | Gln | Ile | Ala | Thr | Ser | Ile | Lys | Gly | Phe | Glu | Asp |
| 225 |     |     |     |     | 230 |     |     |     | 235 |     |     |     |     |     | 240 |
| Val | Pro | Ala | Asn | Asp | Glu | Lys | Ala | Leu | Met | Lys | Ala | Val | Ala | His | His |
|     |     |     |     | 245 |     |     |     |     | 250 |     |     |     |     | 255 |     |
| Pro | Val | Ser | Ile | Gly | Ile | Ala | Gly | Gly | Asp | Ile | Gly | Phe | Gln | Phe | Tyr |
|     |     |     | 260 |     |     |     |     |     | 265 |     |     |     | 270 |     |     |
| Ser | Ser | Gly | Val | Phe | Ser | Gly | Glu | Cys | Thr | Thr | His | Leu | Asp | His | Gly |
|     |     | 275 |     |     |     |     | 280 |     |     |     |     | 285 |     |     |     |
| Val | Thr | Ala | Val | Gly | Tyr | Gly | Arg | Ser | Lys | Asn | Gly | Leu | Lys | Tyr | Trp |
|     | 290 |     |     |     |     | 295 |     |     |     |     | 300 |     |     |     |     |
| Ile | Leu | Lys | Asn | Ser | Trp | Gly | Pro | Lys | Trp | Gly | Glu | Arg | Gly | Tyr | Met |
| 305 |     |     |     |     | 310 |     |     |     | 315 |     |     |     |     |     | 320 |
| Arg | Ile | Lys | Lys | Asp | Ile | Lys | Pro | Lys | His | Gly | Gln | Cys | Gly | Leu | Ala |
|     |     |     | 325 |     |     |     |     | 330 |     |     |     |     | 335 |     |     |
| Met | Asn | Ala | Ser | Tyr | Pro | Thr | Met |     |     |     |     |     |     |     |     |
|     |     |     | 340 |     |     |     |     |     |     |     |     |     |     |     |     |

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:11:

GATGTTTTGT ATGTGGGCCC CTAGGAGATC          30

( 2 ) INFORMATION FOR SEQ ID NO:12:

( i ) SEQUENCE CHARACTERISTICS:
        ( A ) LENGTH: 48 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:12:

GATGTCTTGA GCCTTGTCCT CATCCACATT GATACCAAAC TCCTCCTC          48

( 2 ) INFORMATION FOR SEQ ID NO:13:

( i ) SEQUENCE CHARACTERISTICS:
        ( A ) LENGTH: 43 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:13:

GGAATTCGTC GACAGATCTC TGCAGCTCGA GGGATCCAAG CTT 43

( 2 ) INFORMATION FOR SEQ ID NO:14:

( i ) SEQUENCE CHARACTERISTICS:
        ( A ) LENGTH: 32 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:14:

GCTTGTTCGC CATGGATATC TTCTGTATGT TC 32

( 2 ) INFORMATION FOR SEQ ID NO:15:

( i ) SEQUENCE CHARACTERISTICS:
        ( A ) LENGTH: 29 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:15:

ACTTTCTCAA CTGTCTCTGG TTTAGCAGC 29

( 2 ) INFORMATION FOR SEQ ID NO:16:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

Ala Ala Lys Pro Glu Thr Val Glu Lys Val
 1               5                        10

( 2 ) INFORMATION FOR SEQ ID NO:17:

( i ) SEQUENCE CHARACTERISTICS:
        ( A ) LENGTH: 39 base pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:17:

CTTAAGAAGT AACCCGGGCT GCAGTTTTAG TATTAAGAG 39

SEED-SPECIFIC TRANSCRIPTIONAL REGULATION

This application is a divisional of U.S. application Ser. No. 07/742,834, filed Aug. 8, 1991, U.S. Pat. No. 5,420,034, which is a continuation of U.S. application Ser. No. 07/550,804, filed Jul. 9, 1990, which is a continuation-in-part of U.S. application Ser. No. 07/147,781, filed Jan. 25, 1988 (now abandoned), which is a continuation-in-part of U.S. application Ser. No. 07/078,538, filed Jul. 28, 1987 (now abandoned), which is a continuation in part of U.S. application Ser. No. 06/891,529, filed Jul. 31, 1986 (now abandoned).

INTRODUCTION

1. Technical Field

Genetic modification of plant material is provided for seed-specific transcription. Production of endogenous products may be modulated or new capabilities provided.

2. Background

In general, genetic engineering techniques have been directed to modifying the phenotype of individual prokaryotic and eukaryotic cells, especially in culture. Plant cells have proven more intransigent than other eukaryotic cells due not only to the lack of suitable vector systems but also as a result of the different goals involved. Plant genetic engineering has for the most part been directed to modifying the entire plant or a particular tissue rather than modifying a single cell in culture.

For many applications, it will be desirable to provide for transcription in a particular plant tissue and/or at a particular time in the growth cycle of the plant or maturation cycle of the tissue. Toward this end, there is substantial interest in identifying endogenous plant products whose transcription or expression is regulated in a manner of interest. In identifying such products, one must first look for a product which appears at a particular time in the cell growth cycle or in a particular plant tissue, demonstrate its absence at other times or in other tissue, identify nucleic acid sequences associated with the product and then identify the sequence in the genome of the plant in order to obtain the 5'-untranslated sequence associated with transcription. Identifying the particular sequence, followed by establishing that it is the correct sequence and isolating the desired transcriptional regulatory region requires an enormous outlay in time and effort. One must then prepare appropriate constructs, and demonstrate that the constructs are efficacious in the desired manner.

Identifying such sequences is a challenging project, subject to numerous pitfalls and uncertainty. There is, however, substantial interest in being able to genetically modify plants, which justifies the substantial expenditures and efforts in identifying transcriptional regulatory sequences and manipulating them to determine their utility.

RELEVANT LITERATURE

Crouch et al., In: *Molecular Form and Function of the Plant Genome*, eds. van Vloten-Doting, Groot and Hall, Plenum Publishing Corp. 1985, pp 555–566; Crouch and Sussex, Planta (1981) 153:64–74; Crouch et al., *J. Mol. Appl. Genet.* (1983) 2:273–283; Simon et al., *Plant Molecular Biology* (1985) 5:191–201; and Scofield and Crouch, *J. Biol. Chem.* (1987) 262:12202–12208, describe various aspects of *Brassica napus* storage proteins. Rose et al., *Nucl. Acids Res.* (1987) 15:7197 and Scherer and Knauf, *Plant Mol. Biol.* (1987) 9:127–134 describe ACP genes. Beachy et al., EMBO J. (1985) 4:3047–3053; Sengupta-Gopalan et al., *Proc. Natl. Acad. Sci. USA* (1985) 82:3320–3324; Greenwood and Chrispeels, *Plant Physiol.* (1985) 79:65–71 and Chen et al., *Proc. Natl. Acad. Sci. USA* (1986) 83:8560–8564 describe studies concerned with seed storage proteins and genetic manipulation. Eckes et al., *Mol. Gen. Genet.* (1986) 20.5.:14–22 and Fluhr et al., *Science* (1986) 232:1106–1112 describe the genetic manipulation of light inducible plant genes.

SUMMARY OF THE INVENTION

DNA constructs are provided which are employed in manipulating plant cells to provide for seed-specific transcription. Particularly, transcriptional regions from seed storage proteins, seed coat proteins or acyl carrier protein are joined to other than the homologous gene and introduced into a plant cell host for integration into the genome to provide for seed-specific transcription. The constructs provide for modulation of expression of endogenous products as well as production of exogenous products in the seed.

DESCRIPTION OF THE DRAWINGS

FIGS. 2A, 2B, 2C, 2D, 2E, 2F, 2G, 2H, 2I and 2J are a restriction map of cloned γACGN1-2 showing the entire coding region sequence as well as extensive 5' upstream and 3' downstream sequences (SEQ ID NO: 2). The deduced amino acid sequence of the open reading frame that extends from position 2152 to 2703 is shown in SEQ ID NO:3.

FIGS. 3A, 3B, 3C, 3D and 3E are a partial nucleotide sequence of genomic ACP clone Bcg4—4(SEQ ID NO: 4). The coding region is indicated by the three-letter amino acid codes. Breaks in the coding region sequence represent introns. The underlined nucleotide at position 310 is ambiguous without further sequence analysis for confirmation. The amino acid sequences encoded by exons one (nucleotides 1108 to 1155), two (nucleotides 1462 to 1569), three (nucleotides 1647 to 1769) and four (1855 to 1977) are shown as SEQ ID NO:5, SEQ ID NO:6, SEQ ID NO:7, and SEQ ID NO:8, respectively.

FIGS. 4A, 4B, 4C and 4D are the complete nucleotide sequence of *B. campestris* cDNA EA9 (SEQ ID NO: 9). The longest open reading frame is designated by the three letter amino acid code (SEQ ID. NO. 10). PolyA tails are evident at the end of the sequence and a potential polyadenylation signal is underlined.

DESCRIPTION OF THE SPECIFIC EMBODIMENTS

Figure 1A:
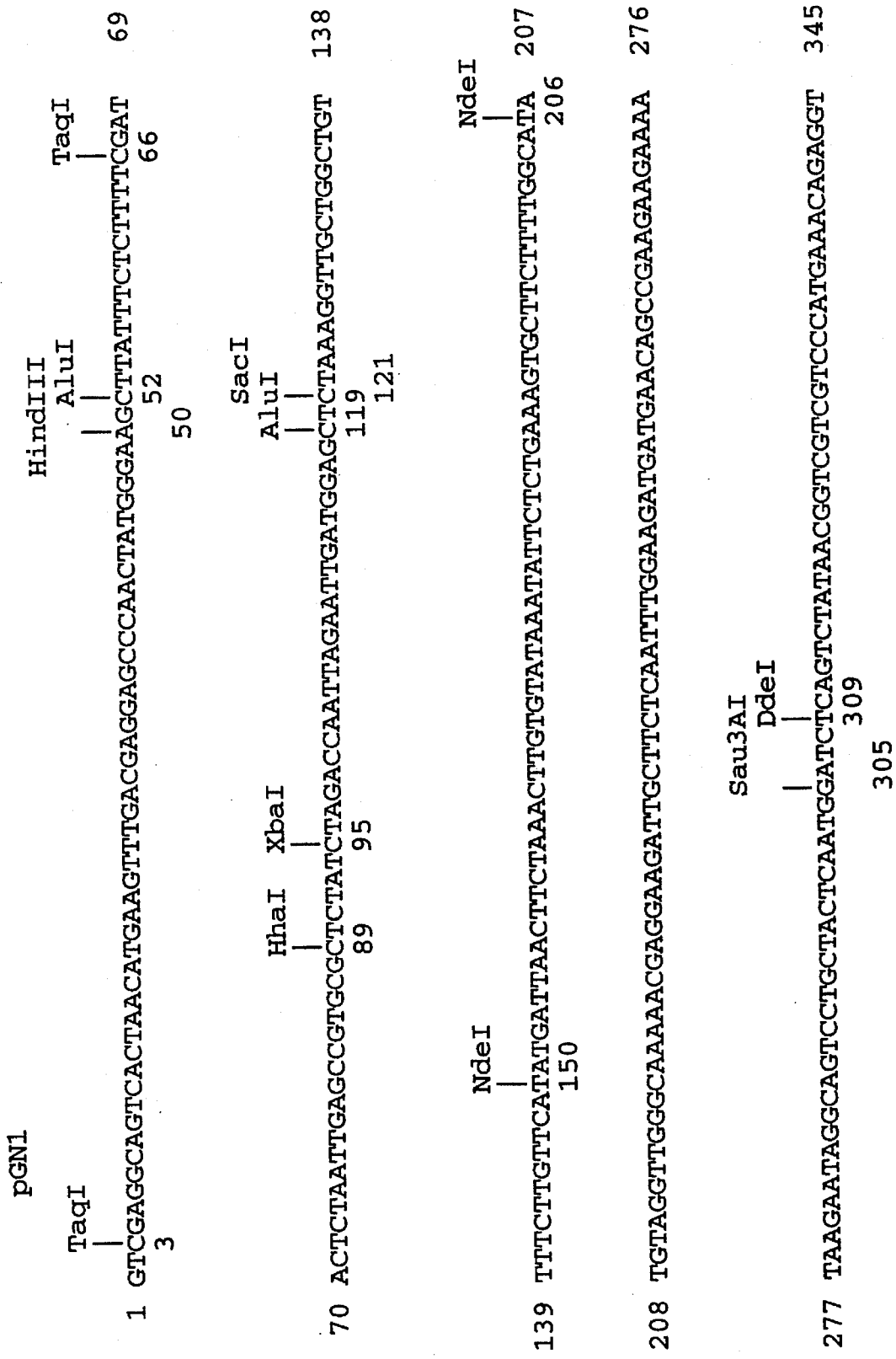
FIG. 1B, 1C, 1D and 1E are a partial sequence of the promoter region of the γBnNa napin gene (SEQ ID NO:1). The start (ATG) of the open reading frame is underlined.

In accordance with the subject invention, novel DNA constructs are provided which allow for modification of transcription in seed, particularly in embryos during seed maturation. The DNA constructs comprise a regulated transcriptional initiation region associated with seed formation, preferably in association with embryogenesis and seed maturation.

Downstream from and under the transcriptional initiation regulation of the seed-specific region will be a sequence of interest which will provide for modification of the phenotype of the seed, by modulating the production of an endogenous product, as to amount, relative distribution, or the like, or production of an exogenous expression product to provide for a novel function or product in the seed. The DNA construct will also provide for a termination region, so as to provide an expression cassette into which a gene may be introduced. Conveniently, transcriptional initiation and termination regions may be provided separated in the direction of transcription by a linker or polylinker having one or a plurality of restriction sites for insertion of the gene to be under the transcriptional regulation of the regulatory regions. Usually, the linker will have from 1 to 10, more usually from about 1 to 8, preferably from about 2 to 6 restriction sites. Generally, the linker will be fewer than 100 bp, frequently fewer than 60 bp and generally at least about 5 bp.

The transcriptional initiation region may be native or homologous to the host or foreign or heterologous to the host. By foreign is intended that the transcriptional initiation region is not found in the wild-type host into which the transcriptional initiation region is introduced.

Of particular interest are those transcriptional initiation regions associated with storage proteins, such as napin, cruciferin, β-conglycinin, phaseolin, or the like, and proteins involved in fatty acid biosynthesis, such as acyl carrier protein (ACP). The transcriptional initiation regions may be obtained from any convenient host, particularly plant hosts such as Brassica, e.g *napus* or *campestris*, soybean (*Glycine max*), bean (*Phaseolus vulgaris*), corn (*Zea mays*), cotton (*Gossypium sp.*), safflower (*Carthamus tinctorius*), tomato (*Lycopersicon esculentum*), and Cuphea species. Other transcriptional initiation regions of particular interest are those associated with seed embryo genes that are expressed in the period from about day 7 to day 40, particularly those having maximum expression in the period from about day 10 to about day 30) postanthesis, and seed coat genes which are expressed in the period from about day 11 to day 30. Usually the period of expression will be at least 3 days, more usually about 7 days and may be substantially over the entire period.

A transcriptional initiation region may be used for varying the phenotype of the seeds. Various changes in phenotype are of interest. These include modifying the fatty acid composition in seeds, that is changing the ratio and/or amounts of the various fatty acids, as to length, unsaturation, or the like. Thus, the fatty acid composition may be varied by enhancing the fatty acids of from 10 to 14 carbon atoms as compared to the fatty acids of from 16 to 18 carbon atoms, increasing or decreasing fatty acids of from 20 to 24 carbon atoms, providing for an enhanced proportion of fatty acids which are saturated or unsaturated, or the like. These results can be achieved by providing for reduction of expression of one or more endogenous products, particularly enzymes or cofactors, by producing a transcription product which is complementary to the transcription product of a native gene, so as to inhibit the maturation and/or expression of the transcription product, or providing for expression of a gene, either endogenous or exogenous, associated with fatty acid synthesis. Expression products associated with fatty acid synthesis include acyl carrier protein, acyl-ACP thioesterase, acetyl-CoA ACP transacylase, acetyl-CoA carboxylase, ketoacyl-ACP synthases, malonyl-CoA ACP transacylase, stearoyl-ACP desaturase, and other desaturase enzymes.

Alternatively, one may provide various products from other sources including mammals, such as blood factors, lymphokines, colony stimulating factors, interferons, plasminogen activators, enzymes, e.g. superoxide dismutase, chymosin, etc., hormones, rat mammary thioesterase 2, phospholipid acyl desaturases involved in the synthesis of eicosapentaenoic acid, human serum albumin. The level of seed proteins, particularly mutated seed proteins, having an improved amino acid distribution which would be better suited to the nutrient value of the seed can also be increased. This can be achieved, for example, by inhibition of the native seed protein by producing a complementary DNA sequence to the native coding region or non-coding region, where the complementary sequence does not hybridize efficiently to the mutated sequence, or inactivates the native transcriptional capability.

The transcriptional cassette will include in the 5'-3' direction of transcription, a transcriptional and translational initiation region, a DNA sequence of interest, and a transcriptional and translational termination region functional in plants. One or more introns may also be present. The DNA sequence may have any open reading frame encoding a peptide of interest, e.g. an enzyme, or a sequence complementary to a genomic sequence, where the genomic sequence may be an open reading frame, an intron, a non-coding leader sequence, or any other sequence where the complementary sequence will inhibit transcription, messenger RNA processing, e.g. splicing, or translation. The DNA sequence of interest may be synthetic, naturally derived, or combinations thereof. Depending upon the nature of the DNA sequence of interest, it may be desirable to synthesize the sequence with plant preferred codons. The plant preferred codons may be determined from the codons of highest frequency in the proteins expressed in the largest amount in the particular plant species of interest.

In preparing the transcription cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, or the like may be employed, where insertions, deletions or substitutions, e.g. transitions and transversions, may be involved.

The termination region which is employed will be primarily one of convenience, since the termination regions appear to be relatively interchangeable. The termination region may be native with the transcriptional initiation region, may be native with the DNA sequence of interest, or may be derived from another source. Convenient termination regions are available from the Ti-plasmid of *A. tumefaciens,* such as the octopine synthase and nopaline synthase termination regions.

By appropriate manipulations, such as restriction, chewing back or filling in overhangs to provide blunt ends, ligation of linkers, or the like, complementary ends of the fragments can be provided for joining and ligation.

In carrying out the various steps, cloning is employed, so as to amplify the amount of DNA and to allow for analyzing the DNA to ensure that the operations have occurred in a proper manner. A wide variety of cloning vectors are available, where the cloning vector includes a replication system functional in *E. coli* and a marker which allows for selection of the transformed cells. Illustrative vectors include pBR332, the pUC series, the M13mp series, pACYC184, etc. Thus, the sequence may be inserted into the vector at an appropriate restriction site(s), the resulting plasmid used to transform the *E. coli* host, the *E. coli* grown in an appropriate nutrient medium and the cells harvested and lysed and the plasmid recovered. Analysis may involve sequence analysis, restriction analysis, electrophoresis, or the like. After each manipulation the DNA sequence to be used in the final construct may be restricted and joined to the next sequence, where each of the partial constructs may be cloned in the same or different plasmids.

Depending upon the manner of introduction of the transcription construct into the host plant, other DNA sequences may be required. For example, when using the Ti- or Ri-plasmid for transformation of plant cells, as described below, at least the right border and frequently both the right and left borders of the T-DNA of the Ti- and Ri-plasmids will be joined as flanking regions to the transcription construct. The use of T-DNA for transformation of plant cells has received extensive study and is amply described in EPA Serial No. 120,516, Hoekema, In: The Binary Plant Vector System Offset-drukkerij Kanters B.V., Alblasserdam, 1985, Chapter V, Fraley, et al., *Crit. Rev. Plant Sci.*, 4:1–46, and An et al., EMBO J. (1985) 4:277–284.

Alternatively, to enhance integration into the plant genome, terminal repeats of transposons may be used as borders in conjunction with a transposase. In this situation, expression of the transposase should be inducible, or the transposase inactivated, so that once the transcription construct is integrated into the genome, it should be relatively stably integrated to avoid hopping.

The transcription construct will normally be joined to a marker for selection in plant cells. Conveniently, the marker may be resistance to a biocide, particularly an antibiotic, such as kanamycin, G418, bleomycin, hygromycin, chloramphenicol, or the like. The particular marker employed will be one which will allow for selection of transformed cells as compared to cells lacking the DNA which has been introduced.

A variety of techniques are available for the introduction of DNA into a plant cell host. These techniques include transformation with Ti-DNA employing *A. tumefaciens* or *A. rhizoenes* as the transforming agent, protoplast fusion, injection, electroporation, etc. For transformation with Agrobacterium, plasmids can be prepared in *E. coli* which plasmids contain DNA homologous with the Ti-plasmid, particularly T-DNA. The plasmid may or may not be capable of replication in Agrobacterium, that is, it may or may not have a broad spectrum prokaryotic replication system, e.g. RK290, depending in part upon whether the transcription construct is to be integrated into the Ti-plasmid or be retained on an independent plasmid. By means of a helper plasmid, the transcription construct may be transferred to the *A. tumefaciens* and the resulting transformed organism used for transforming plant cells.

Conveniently, explants may be cultivated with *A. tumefaciens* or *A. rhizogenes* to allow for transfer of the expression cassette to the plant cells, the plant cells dispersed in an appropriate selective medium for selection, grown to callus, shoots grown and plantlets regenerated from the shoots by growing in rooting medium. The Agrobacterium host will contain a plasmid having the vir genes necessary for transfer of the T-DNA to the plant cells and may or may not have T-DNA. For injection and electropotation, disarmed Ti-plasmids (lacking the tumor genes, particularly the T-DNA region) may be used to introduce genes into the plant cell.

The cells which have been transformed may be grown into plants in accordance with conventional ways. See, for example, McCormick et al., *Plant Cell Reports* (1986) 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

As a host cell, any plant variety may be employed which provides a seed of interest. Thus, for the most part, plants will be chosen where the seed is produced in high amounts or a seed-specific product of interest is involved. Seeds of interest include the oil seeds, such as the Brassica seeds, cotton seeds, soybean, safflower, sunflower, or the like; grain seeds, e.g. wheat, barley, rice, clover, corn, or the like.

Identifying useful transcriptional initiation regions may be achieved in a number of ways. Where a seed protein has been or is isolated, it may be partially sequenced, so that a probe may be designed for identifying messenger RNA specific for seed. To further enhance the concentration of the messenger RNA specifically associated with seed, cDNA may be prepared and the cDNA subtracted with messenger RNA or cDNA from non-seed associated cells. The residual cDNA may then be used for probing the genome for complementary sequences, using an appropriate library prepared from plant cells. Sequences which hybridize to the cDNA may then be isolated, manipulated, and the 5'-untranslated region associated with the coding region isolated and used in expression constructs to identify the transcriptional activity of the 5'-untranslated region.

In some instances, a probe may be employed directly for screening a genomic library and identifying sequences which hybridize to the probe. The sequences will be manipulated as described above to identify the 5'-untranslated region.

The expression constructs which are prepared employing the 5'-untranslated regions may be transformed into plant cells as described previously for evaluation of their ability to function with a heterologous structural gene (i.e., a gene other than the open reading frame associated with the 5'-untranslated region) and the seed-specificity. In this manner, specific sequences may be identified for use with sequences for seed-specific transcription. Of particular interest are transcriptional initiation regions from napin genes, particularly Brassica napin genes, more particularly *Brassica napus* or *Brassica campestris* genes; transcriptional initiation regions regulating structural genes associated with lipid production, particularly fatty acid production, including acyl carrier proteins, which may be endogenous or exogenous to the particular plant, such as spinach acyl carrier protein, Brassica acyl carrier protein (either *napus* or *campestris*), Cuphea acyl carrier protein, acetyl-CoA ACP transacylase, malonyl-CoA ACP transacylase, β-ketoacyl-ACP synthases I and II, acyl-ACP thioesterase, particularly thioesterase II, from plant, mammalian, or bacterial sources, for example rat thioesterase II, acyl ACP, or phospholipid acyl desaturases.

The following examples are offered by way of illustration and not by way of limitation.

EXPERIMENTAL

Materials and Methods

Cloning Vectors

Cloning vectors used include the pUC vectors, pUC8 and pUC9 (Vieira and Messing, Gene (1982) 19:259–268); pUC18 and pUC19 (Norrander et al., Gene (1983)

26:101–106; Yanisch-Perron et al., Gene (1985) 33:103–119), and analogous vectors exchanging chloramphenicol resistance (CAM) as a marker for the ampicillin resistance of the pUC plasmids described above (pUC-CAM [pUC12-Cm, pUC13-Cm] Buckley, K., Ph.D. Thesis, U.C.S.D., Calif. 1985). The multiple cloning sites of pUC18 and pUC19 vectors were exchanged with those of pUC-CAM to create pCGN565 and pCGN566 which are CAM resistant. Also used were pUC118 and pUC119, which are respectively, pUC18 and pUC19 with the intergenic region of M13, from an HgiAI site at 5465 to the AhaIII site at 5941, inserted at the NdeI site of pUC (available from Vieira J. and Messing, J. Waksman Institute, Rutgers University, Rutgers, N.J.)

Materials

Terminal deoxynucleotide transferase (TDT), RNaseH, *E. coli* DNA polymerase, T4 kinase, and restriction enzymes were obtained from Bethesda Research Laboratories; *E. coli* DNA ligase was obtained from New England Biolabs; reverse transcriptase was obtained from Life Sciences, Inc.; isotopes were obtained from Amersham; X-gal was obtained from Bachem, Inc. Torrance, Calif.

EXAMPLE I

Construction of a Napin Promoter

There are 298 nucleotides upstream of the ATG start codon of the napin gene on the pgN1 clone, a 3.3 kb EcoRI fragment of *B. napus* genomic DNA containing a napin gene cloned into pUC8 (available from Marti Crouch, University of Indiana). pgN1 DNA was digested with EcoRI and SstI and ligated to EcoRI/SstI digested pCGN706. (pCGN706 is an XhoI/PstI fragment containing 3' and polyadenylation sequences of another napin cDNA clone pN2 (Crouch et al., 1983 supra) cloned in pCGN566 at the SalI and PstI sites.) The resulting clone pCGN707 was digested with SalI and treated with the enzyme Bal31 to remove some of the coding region of the napin gene. The resulting resected DNA was digested with SmaI after the Bal31 treatment and religated. One of the clones, pCGN713, selected by size, was subcloned by EcoRI and BamHI digestion into both EcoRI-BamHI digested pEMBL18 (Dente et al., *Nucleic Acids Res.* (1983) 11:1645–1655) and pUC118 to give E418 and E4118 respectively. The extent of Bal31 digestion was confirmed by Sanger dideoxy sequencing of E418 template. The Bal31 deletion of the promoter region extended only to 57 nucleotides downstream of the start codon, thus containing the 5' end of the napin coding sequence and about 300 bp of the 5' non-coding region. E4118 was tailored to delete all of the coding region of napin including the ATG start codon by in vitro mutagenesis by the method of Zoller and Smith (*Nucleic Acids Res.* (1982) 10:6487–6500) using an oligonucleotide primer (SEQ ID NO: 11) 5'-GATGTTTTGTAT-GTGGGCCCCTAGGAGATC-3'. Screening for the appropriate mutant was done by two transformations into *E. coli* strain JM83 (Messing J., In: Recombinant DNA Technical Bulletin, NIH Publication No. 79–99, 2 No. 2, 1979, pp 43–48) and SmaI digestion of putative transformants. The resulting napin promoter clone is pCGN778 and contains 298 nucleotides from the EcoRI site of pgN1 to the A nucleotide just before the ATG start codon of napin. The promoter region was subcloned into a chloramphenicol resistant background by digestion with EcoRI and BamHI and ligation to EcoRI-BamHI digested pCGN565 to give pCGN779c.

Figure 1B:
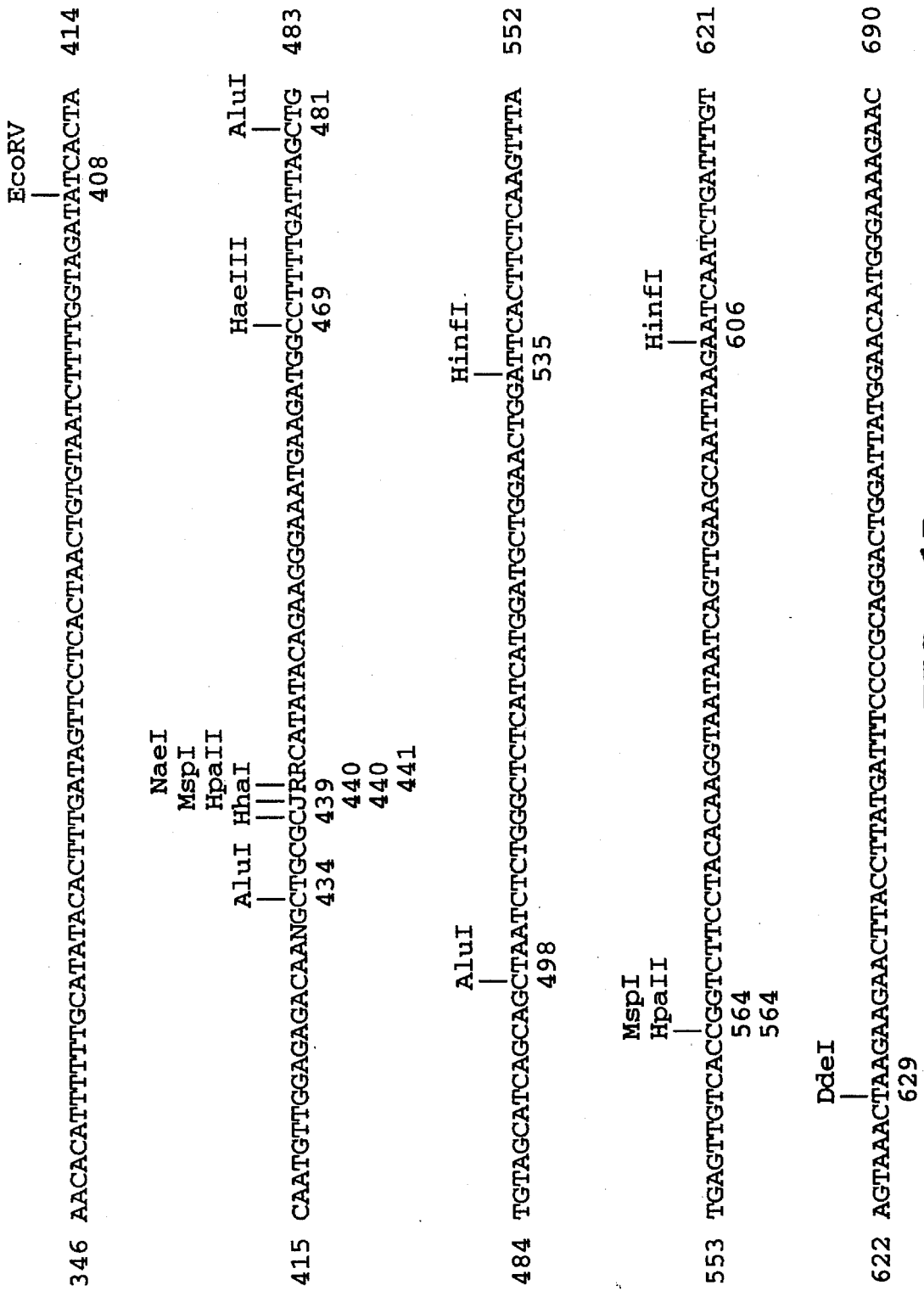
Figure 1C:
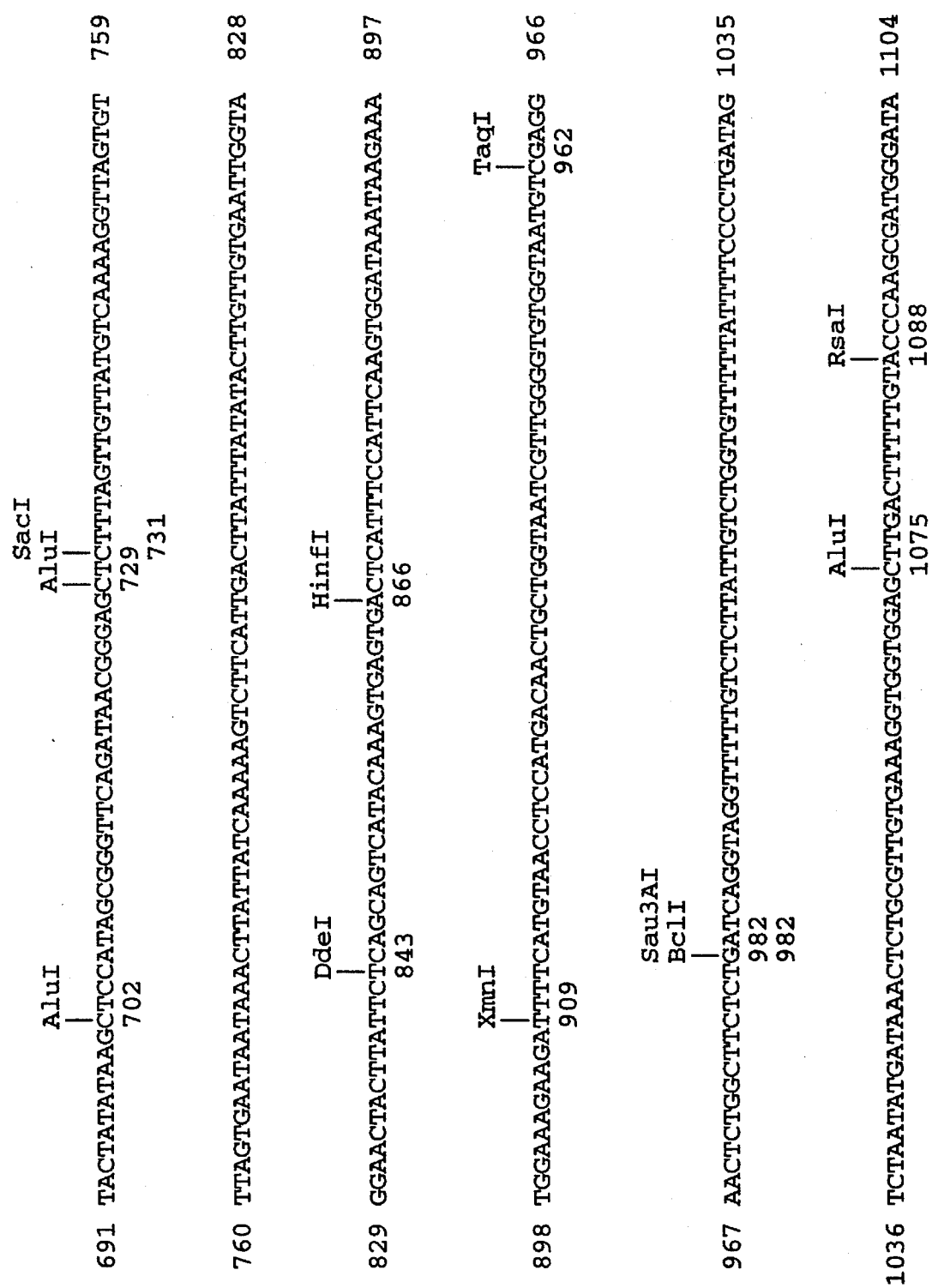
Figure 1E:
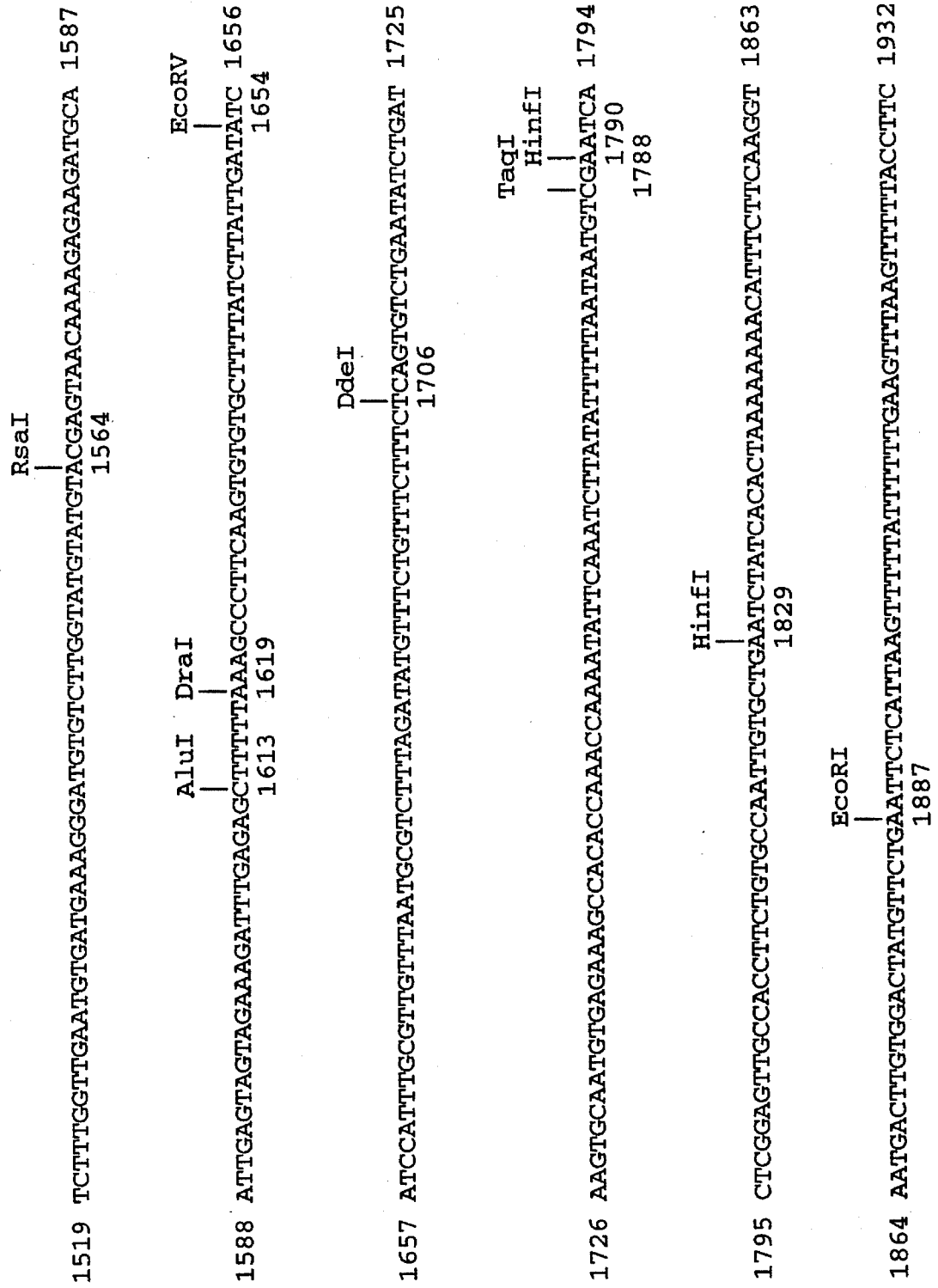
Figure 1F:
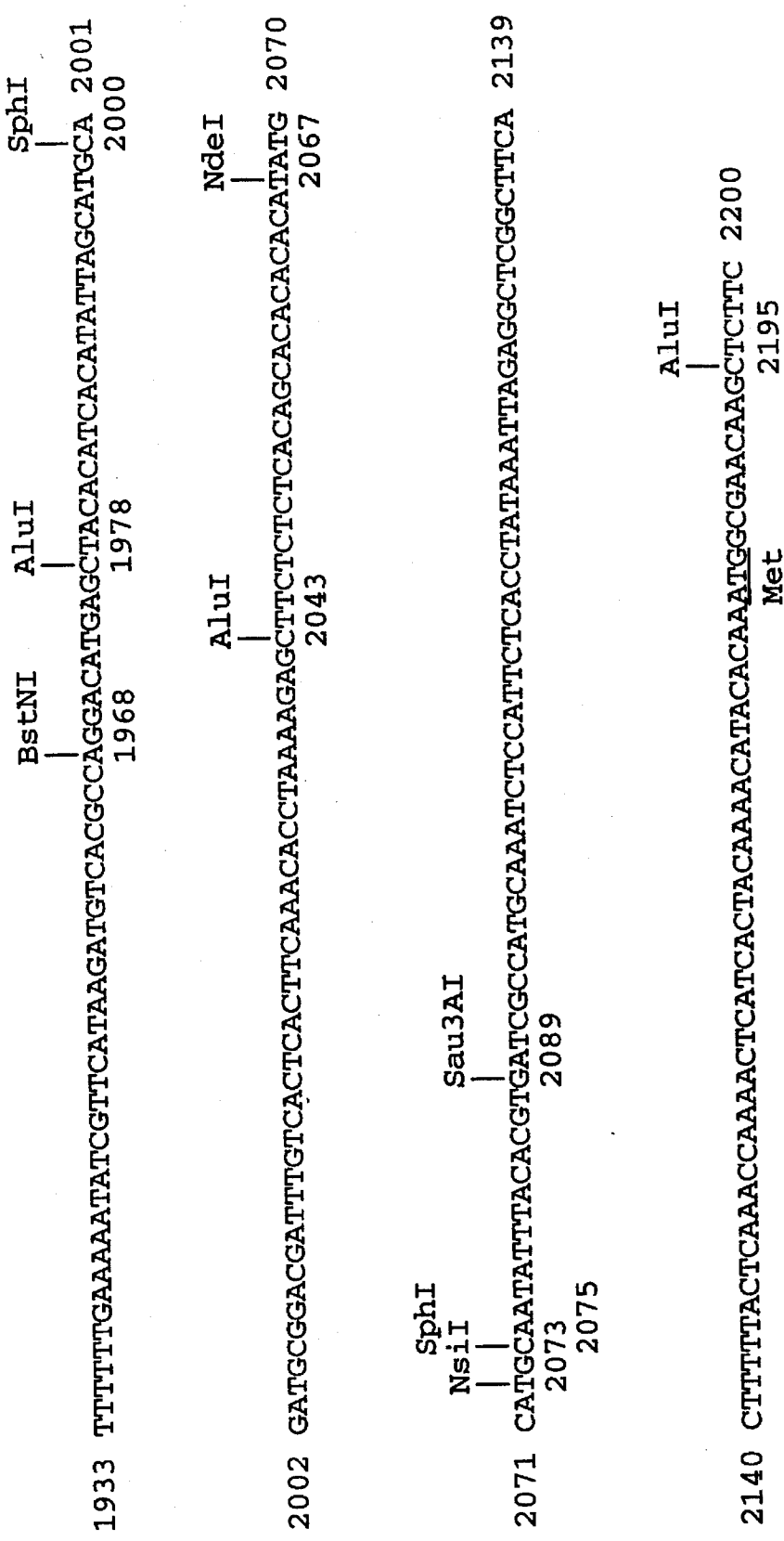

Extension of the Napin Promoter Clone pCGN779c contains only 298 nucleotides of potential 5'-regulatory sequence. The napin promoter was extended with a 1.8 kb fragment found upstream of the 5'-EcoRI site on the original γBnNa clone. The –3.5 kb XhoI fragment of γBnNa (available from M. Crouch), which includes the napin region, was subcloned into SalI-digested pUC119 to give pCGN930. A HindIII site close to a 5' XhoI site was used to subclone the HindIII-EcoRI fragment of pCGN930 into HindIII-EcoRI digested Bluescript +(Vector Cloning Systems, San Diego, Calif.) to give pCGN942. An extended napin promoter was made by ligating pCGN779c digested with EcoRI and PstI and pCGN942 digested with EcoRI and PstI to make pCGN943. This promoter contains –2.1 kb of sequence upstream of the original ATG of the napin gene contained on γBnNa. A partial sequence of the promoter region is shown in FIGS. 1A, 1B, 1C, 1D and 1E.

Napin Cassettes

The extended napin promoter and a napin 3'-regulatory region are combined to make a napin cassette for expressing genes seed-specifically. The napin 3'-region used is from the plasmid pCGN1924 containing the XhoI-EcoRI fragment from pgN1 (XhoI site is located 18 nucleotides from the stop codon of the napin gene) subcloned into EcoRI-SalI digested pCGN565. HindIII-PStI digested pCGN943 and pCGN1924 are ligated to make the napin cassette pCGN944, with unique cloning sites SmaI, SalI, and PstI for inserting genes.

Construction of cDNA Library from Spinach Leaves

Total RNA was extracted from young spinach leaves in 4M guanidine thiocyanate buffer as described by Facciotti et al. (*Biotechnology* (1985) 3:241–246). Total RNA was subjected to oligo(dT)-cellulose column chromatography two times to yield poly(A)$^+$RNA as described by Maniatis et al., (1982) *Molecular Cloning: A Laboratory Manual,* Cold Spring Harbor Laboratory, N.Y. A cDNA library was constructed in pUC13-Cm according to the method of Gubler and Hoffman, (Gene (1983) 25:263–269) with slight modifications. RNasin was omitted in the synthesis of first strand cDNA as it interfered with second strand synthesis if not completely removed, and dCTP was used to tail the vector DNA and dGTP to tail double-stranded cDNA instead of the reverse as described in the paper. The annealed cDNA was transformed to competent *E. coli* JM83 (Messing (1979) supra) cells according to Hanahan (*J. Mol. Biol.* (1983) 166:557–580 ) and spread onto LB agar plates (Miller (1972) Experiments in Molecular Genetics. Cold Spring Harbor Laboratory, Cold Spring Harbor, N.Y.) containing 50 μg/ml chloramphenicol and 0.005% X-Gal.

Identification of Spinach ACP-I cDNA

A total of approximately 8000 cDNA clones were screened by performing Southern blots (Southern, *J. Mol. Biol.* (1975) 98:503)and dot blot (described below) hybridizations with clone analysis DNA from 40 pools representing 200 cDNA clones each (see below). A 5' end-labeled synthetic oligonucleotide (ACPP4) that is at least 66% homologous with a 16 amino acid region of spinach ACP-I (SEQ ID NO: 12) (5'-GATGTCTTGAGCCTTGTCCT-CATCCACATTGATACCAAACTCCTCCTC-3') is the complement to a DNA sequence that could encode the 16 amino acid peptide glu-glu-glu-phe-gly-ile-asn-val-asp-gluasp-lys-ala-gln -asp-ile, residues 49–64 of spinach ACP-I (Kuo and Ohlrogge, *Arch. Biochem. Biophys.* (1984) 234:290–296) and was used for an ACP probe.

Clone analysis DNA for Southern and dot blot hybridizations was prepared as follows. Transformants were transferred from agar plates to LB containing 50 μg/ml chloramphenicol in groups of ten clones per 10 ml media. Cultures were incubated overnight in a 37° C. shaking incubator and then diluted with an equal volume of media and allowed to grow for 5 more hours. Pools of 200 cDNA clones each were obtained by mixing contents of 20 samples. DNA was extracted from these cells as described by Birnboim and Doly (*Nucleic Acids Res.* (1979) 7:1513–1523). DNA was purified to enable digestion with restriction enzymes by extractions with phenol and chloroform followed by ethanol precipitation. DNA was resuspended in sterile, distilled water and 1 μg of each of the 40 pooled DNA samples was digested with EcoRI and HindIII and electrophoresed through 0.7% agarose gels. DNA was transferred to nitrocellulose filters following the blot hybridization technique of Southern.

ACPP4 was 5' end-labeled using $\gamma$-$^{32}$P dATP and T4 kinase according to the manufacturer's specifications. Nitrocellulose filters from Southern blot transfer of clone analysis DNA were hybridized (24 hours, 42° C.) and washed according to Berent et al. (*BioTechniques* (1985) 3:208–220). Dot blots of the same set of DNA pools were prepared by applying 1 μg of each DNA pool to nylon membrane filters in 0.5M NaOH. These blots were hybridized with the probe for 24 hours at 42° C. in 50% formamide/1% SDS/1M NaCl, and washed at room temperature in 2X SSC/0.1% SDS (1X SSC=0.15M NaCl; 0.015M Na citrate; SDS-sodium dodecylsulfate). DNA from the pool which was hybridized by the ACPP4 oligoprobe was transformed to JM83 cells and plated as above to yield individual transformants. Dot blots of these individual cDNA clones were prepared by applying DNA to nitrocellulose filters which were hybridized with the ACPP4 oligonucleotide probe and analyzed using the same conditions as for the Southern blots of pooled DNA samples.

Nucleotide Sequence Analysis

The positive clone, pCGN1SOL, was analyzed by digestion with restriction enzymes and the following partial map was obtained.

pCGN1SOL contains an (approximately) 700 bp cDNA insert including a stretch of A residues at the 3' terminus which represents the poly(A) tail of the mRNA. An ATG codon at position 61 is presumed to encode the MET translation initiation codon. This codon is the start of a 411 nucleotide open reading frame, of which, nucleotides 229–471 encode a protein whose amino acid sequence corresponds almost perfectly with the published amino acid sequence of ACP-I of and Ohlrogge supra as described previously. In addition to mature protein, the pCGN1SOL also encodes a 56 residue transit peptide sequence, as might be expected for a nuclearencoded chloroplast protein.

Napin-ACP Construct pCGN796 was constructed by ligating pCGN1SOL digested with HindIII-BamHI, pUC8-CM digested with HindIII and BamHI and pUC118 digested with BamHI. The ACP gene from pCGN796 was transferred into a chloramphenicol background by digestion with BamHI and ligation with BamHI digested pCGN565. The resulting pCGN1902 was digested with EcoRI and SmaI and ligated to EcoRI-SmaI digested pUC118 to give pCGN1920. The ACP gene in pCGN1920 was digested at the NcoI site, filled in by treatment with the Klenow fragment, digested with SmaI and religated to form pCGN1919. This eliminated the 5'-coding sequences from the ACP gene and regenerated the ATG. This ACP gene was flanked with PstI sites by digesting pCGN1919 with EcoRI, filling in the site with the Klenow fragment and ligating a PstI linker. This clone is called pCGN945.

The ACP gene of pCGN945 was moved as a BamHI-PstI fragment to pUC118 digested with BamHI and PstI to create pCGN945a so that a SmaI site (provided by the pUC118) would be at the 5'-end of the ACP sequences to facilitate cloning into the napin cassette pCGN944. pCGN945a digested with SmaI and PstI was ligated to pCGN944 digested with SmaI and PstI to produce the napin ACP cassette pCGN946. The napin ACP cassette was then transferred into the binary vector pCGN783 by cloning from the HindIII site to produce pCGN948.

Construction of the Binary Vector pCGN783 pCGN783 is a binary plasmid containing the left and right T-DNA borders of *A. tumefaciens* (Barker et al., *Plant Mol. Biol.* (1983) 2:335–350); the gentamicin resistance gene of

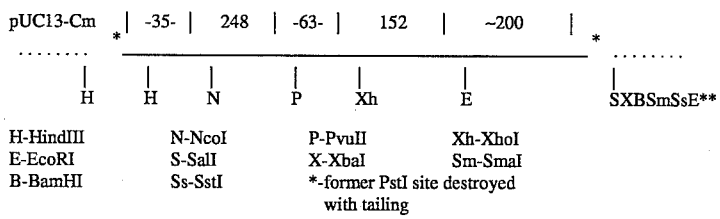

```
pUC13-Cm  * | -35- |  248  | -63- |  152  | ~200  |  *
........  _____   ........
            |      |   |    |     |       |
            H      H   N    P     Xh      E              SXBSmSsE**

H-HindIII       N-NcoI         P-PvuII        Xh-XhoI
E-EcoRI         S-SalI         X-XbaI         Sm-SmaI
B-BamHI         Ss-SstI        *-former PstI site destroyed
                                 with tailing
```

**polylinker with available restriction sites indicated

The cDNA clone was subcloned into pUC118 and pUC119 using standard laboratory techniques of restriction, ligation, transformation, and analysis (Maniatis et al., (1982) supra). Single-stranded DNA template was prepared and DNA sequence was determined using the Sanger dideoxy technique (Sanger et al., *Proc. Nat. Acad. Sci. USA* (1977) 74:5463–5467). Sequence analysis was performed using a software package from Intelli-Genetics, Inc.

pPH1 JI (Hirsch et al., *Plasmid* (1984), 12:139–141) the 35S promoter of cauliflower mosaic virus (CaMV) (Gardner et al., *Nucleic Acids Res.* (1981) 9:2871–2890), the kanamycin resistance gene of Tn5 (Jorgenson et al., infra and Wolff et al., *Nucleic Acids Res.* (1985) 13:355–367) and the 3' region from transcript 7 of pTiA6 (Barker et al., (1983) Supra).

To obtain the gentamicin resistance marker, the gentamicin resistance gene was isolated as a 3.1 kb EcoRI-PstI fragment of pPHIJ1 cloned into pUC9 yielding pCGN549.

The HindIII-BamHI fragment containing the gentamicin resistance gene was substituted for the HindIII-BglII fragment of pCGN587 creating pCGN594.

pCGN587 was prepared as follows: The HindIII-SmaI fragment of Tn5 containing the entire structural gene for APHII (Jorgenson et al., *Mol. Gen. Genet.* (1979) 177:65) was cloned into pUC8 (Vieira and Messing, Gene (1982) 19:259), converting the fragment into a HindIII-EcoRI fragment, since there is an EcoRI site immediately adjacent to the SmaI site. The PstI-EcoRI fragment containing the 3'-portion of the APHII gene was then combined with an EcoRI-BamHI-SalI-PstI linker into the EcoRI site of pUC7 (pCGN54'6W). Since this construct does not confer kanamycin resistance, kanamycin resistance was obtained by inserting the BglII-PstI fragment of the APHII gene into the BamHI-PstI site (pCGN546X). This procedure reassembles the APHII gene, so that EcoRI sites flank the gene. An ATG codon was upstream from and out of reading frame with the ATG initiation codon of APHII. The undesired ATG was avoided by inserting a Sau3A-pstI fragment from the 5'-end of APHII, which fragment lacks the superfluous ATG, into the BamHI-PstI site of pCGN546W to provide plasmid pCGN550.

The EcoRI fragment containing APHII gene was then cloned into the unique EcoRI site of pCGN451, which contains an octopine synthase cassette for expression, to provide pCGN552 (1ATG).

pCGN451 includes an octopine cassette which contains about 1556 bp of the 5' non-coding region fused via an EcoRI linker to the 3' non-coding region of the octopine synthase gene of pTiA6. The pTi coordinates are 11,207 to 12,823 for the 3' region and 13,643 to 15,208 for the 5' region as defined by Barker et al., *Plant Mol. Biol.* (1983) 2:325.

The 5' fragment was obtained as follows. A small subcloned fragment containing the 5' end of the coding region, as a BamHI-EcoRI fragment was cloned in pBR322 as plasmid pCGN407. The BamHI-EcoRI fragment has an XmnI site in the coding region, while pBR322 has two XmnI sites. pCGN407 was digested with XmnI, resected with Bal31 nuclease and EcoRI linkers added to the fragments. After EcoRI and BamHI digestion, the fragments were size fractionated, the fractions cloned and sequenced. In one case, the entire coding region and 10 bp of the 5' non-translated sequences had been removed leaving the 5' non-translated region, the mRNA cap site and 16 bp of the 5' non-translated region (to a BamHI site) intact. This small fragment was obtained by size fractionation on a 7% acrylamide gel and fragments approximately 130 bp long eluted.

This size fractionated DNA was ligated into M13mp9 and several clones sequenced and the sequence compared to the known sequence of the octopine synthase gene. The M13 construct was designated p14, which plasmid was digested with BamHI and EcoRI to provide the small fragment which was ligated to a XhoI to BamHI fragment containing upstream 5' sequences from pTiA6 (Garfinkel and Nester, *J. Bacteriol.* (1980) 144:732) and to an EcoRI to XhoI fragment containing the 3' sequences.

The resulting XhoI fragment was cloned into the XhoI site of a pUC8 derivative, designated pCGN426. This plasmid differs from pUC8 by having the sole EcoRI site filled in with DNA polymerase I, and having lost the PstI and HindIII site by nuclease contamination of HincII restriction endonuclease, when a XhoI linker was inserted into the unique HincII site of pUC8. The resulting plasmid pCGN451 has a single EcoRI site for the insertion of protein coding sequences between the 5' non-coding region (which contains 1,550 bp of 5' non-transcribed sequence including the right border of the T-DNA, the mRNA cap site and 16 bp of 5'non-translated sequence) and the 3' region (which contains 267 bp of the coding region, the stop codon, 196 bp of 3' non-translated DNA, the polyA site and 1,153 bp of 3' non-transcribed sequence). pCGN451 also provides the right T-DNA border.

The resulting plasmid pCGN451 having the ocs 5' and the ocs 3' in the proper orientation was digested with EcoRI and the EcoRI fragment from pCGN551 containing the intact kanamycin resistance gene inserted into the EcoRI site to provide pCGN552 having the kanamycin resistance gene in the proper orientation.

This ocs/KAN gene was used to provide a selectable marker for the trans type binary vector pCGN587.

The 5' portion of the engineered octopine synthase promoter cassette consists of pTiA6 DNA from the XhoI at bp 15208–13644 (Barker's numbering), which also contains the T-DNA boundary sequence (border) implicated in T-DNA transfer. In the plasmid pCGN587, the ocs/KAN gene from pCGN552 provides a selectable marker as well as the right border. The left boundary region was first cloned in M13mp9 as a HindIII-SmaI piece (pCGN502) (base pairs 602–2213) and recloned as a KpnI-EcoRI fragment in pCGN565 to provide pCGN580. pCGN565 is a cloning vector based on pUC8-Cm, but containing pUC18 linkers. pCGN580 was linearized with BamHI and used to replace the smaller BlII fragment of pVCK102 (Knauf and Nester, Plasmid (1982) 8:45), creating pCGN585. By replacing the smaller SalI fragment of pCGN585 with the XhoI fragment from pCGN552 containing the ocs/KAN gene, pCGN587 was obtained.

The pCGN594 HindIII-BamHI region, which contains an 5'-ocs-kanamycin-ocs-3' (ocs is octopine synthase with 5' designating the promoter region and 3' the terminator region, see U.S. application Ser. No. 775,923, filed Sep. 13, 1985) fragment was replaced with the HindIII-BamHI polylinker region from pUC18.

pCGN566 contains the EcoRI-HindIII linker of pUC18 inserted into the EcoRI-HindIII sites of pUC13-Cm. The HindIII-BglII fragment of pNW31C-8,29-1 (Thomashow et al., Cell (1980) 19:729) containing ORF1 and −2 of pTiA6 was subcloned into the HindIII-BamHI sites of pCGN566 producing pCGN703.

The Sau3A fragment of pCGN703 containing the 3' region of transcript 7 (corresponding to bases 2396–2920 of pTiA6 (Barker et al., (1983) supra) was subcloned into the BamHI site of pUC18 producing pCGN709. The EcoRI-SmaI polylinker region of pCGN709 was substituted with the EcoRI-SmaI fragment of pCGN587, which contains the kanamycin resistance gene (APH3-II) producing pCGN72 6.

The EcoRI-SalI fragment of pCGN726 plus the BlII-EcoRI fragment of pCGN734 were inserted into the BamHI-SalI site of pUC8-Cm producing pCGN738. pCGN726c is derived from pCGN738 by deleting the 900 p EcoR-EcoRI fragment.

To construct pCGN167, the AluI fragment of CaMV (bp 7144-7735) (Gardner et al., *Nucl. Acid Res.* (1981) 9:2871–2888) was obtained by digestion with AluI and cloned into the HincII site of M13mp7 (Messing et al., *Nucl. Acids Res.* (1981) 9:309–321 ) to create C614. An EcoRI digest of C61 4 produced the EcoRI fragment from C614 containing the 35promoter which was cloned into the EcoRI site-of pUC8 (Vieira and Messing, Gene (1982) 19:259) to produce pCGN146.

To trim the promoter region, the BglII site (bp 7670) was treated with BglII and resected with Bal31 and subsequently a BglII linker was attached to the Bal31 treated DNA to produce pCGN147.

pCGN148a containing a promoter region, selectable marker (KAN with 2 ATG's) and 3' region, was prepared by digesting pCGN528 with BglII and inserting the BamHI-BglII promoter fragment from pCGN147. This fragment was cloned into the BglII site of pCGN528 so that the BglII site was proximal to the kanamycin gene of pCGN528.

The shuttle vector used for this construct, pCGN528, was made as follows. pCGN525 was made by digesting a plasmid containing Tn5 which harbors a kanamycin gene (Jorgenson et al., *Mol. Gen. Genet.* (1979) 177:65 ) with HindIII-BamHI and inserting the HindIII-BamHI fragment containing the kanamycin gene into the HindIII-BamHI sites in the tetracycline gene of pACYC184 (Chang and Cohen, J. Bacteriol. (1978) 134: 1141–1156). pCGN526 was made by inserting the BamHI fragment 19 of pTiA6 (Thomashow et al., Cell (1980) 19:729–739), modified with XhoI linkers inserted into the SmaI site, into the BamHI site of pCGN525. pCGN528 was obtained by deleting the small XhoI fragment from pCGN526 by digesting with XhoI and religating. pCGN149a was made by cloning the BamHI-kanamycin gene fragment from pMB9KanXXI into the BamHI site of pCGN148a.

pMB9KanXXI is a pUC4K variant (Vieira and Messing, Gene (1982) 19:259–268)which has the XhoI site missing but contains a functional kanamycin gene from Tn903 to allow for efficient selection in Agrobacterium.

pCGN149a was digested with BglII and SphI. This small BglII-I fragment of pCGN149a was replaced with the BamHI-SphI fragment from MI (see below) isolated by digestion with BamHI and SphI. This produces pCGN167, a construct containing a full length CaMV promoter, 1ATG-kanamycin gene, 3' end and the bacterial Tn903-type kanamycin gene. MI is an EcoRI fragment from pCGN546X (see construction of pCGN587) and was cloned into the ECoRI cloning site of M13mp9 in such a way that the pstI site in the 1ATG-kanamycin gene was proximal to the polylinker region of M13mp9.

The HindIII-BamHI fragment in the pCGN167 containing the CaMV-35S promoter, 1ATG-kanamycin gene and the BamHI-fragment 19 of pTiA6 was cloned into the BamHI-HindIII sites of pUC19 creating pCGN976. The 35S promoter and 3' region from transcript 7 was developed by inserting a 0.7 kb HindIII-EcoRI fragment of pCGN976 (35S promoter) and the 0.5 kb EcoRI-SalI fragment of pCGN709 (transcript 7:3') into the HindIII-SalI sites of pCGN566 creating pCGN766c.

The 0.7 kb HindIII-EcoRI fragment of pCGN766c (CaMV-35S promoter) was ligated to the 1.5 kb EcoRI-SalI fragment in pCGN726c (1ATG-KAN 3' region) followed by insertion into the HindIII-SalI sites of pUC119 to produce pCGN778. The 2.2 kb region of pCGN778, HindIII-SalI fragment containing the CaMV-35S promoter and 1ATG-KAN-3' KAN-3' region was used to replace the HindIII-SalI linker region of pCGN739 to produce pCGN783.

Transfer of the Binary Vector pCGN948 into *Agrobacterium* pCGN948 was introduced into *Agrobacterium tumefaciens* EHA1 01 (Hood et al., *J. Bacteriol.* (1986) 68:1291–1301 ) by transformation. An overnight 2 ml culture of EHA101 was grown in MG/L broth at 30° C. 0.5 ml was inoculated into 100 ml of MG/L broth (Garfinkei and Nester, *J. Bacteriol.* (1980) 144:732–743 ) and grown in a shaking incubator for 5 h at 30° C. The cells were pelleted by centrifugation at 7K, resuspended in 1 ml of MG/L broth and placed on ice. Approximately, 1 μg of pCGN948 DNA was placed in 100 μl of MG/L broth to which 200 μl of the EHA101 suspension was added; the tube containing the DNA-cell mix was immediately placed into a dry ice/ethanol bath for 5 minutes. The tube was quick thawed by 5 minutes in 37° C. water bath followed by 2 h of shaking at 30° C. after adding 1 ml of fresh MG/L medium. The cells were pelleted and spread onto MG/L plates (1.5% agar ) containing 100 mg/l gentamicin. Plasmid DNA was isolated from individual gentamicin-resistant colonies, transformed back into *E. coli*, and characterized by restriction enzyme analysis to verify that the gentamicin-resistant EHA101 contained intact copies of pCGN948. Single colonies are picked and purified by two more streakings on MG/L plates containing 100 mg/l gentamicin.

Transformation and Regeneration of B. Napus

Seeds of *Brassica napus* cv Westar were soaked in 95% ethanol for 4 minutes. They were sterilized in 1% solution of sodium hypochlorite with 50 μl of "Tween 20" surfactant per 100 ml sterile solution. After soaking for 45 minutes, seeds were rinsed 4 times with sterile distilled water. They were planted in sterile plastic boxes 7 cm wide, 7 cm long, and 10 cm high (Magenta) containing 50 ml of 1/10th concentration of MS (Murashige minimal organics medium, Gibco) with added pyrldoxine (50 μg/l), nicotinic acid (50 μg/l), glycine (200 μg/l) and solidified with 0.6% agar. The seeds germinated and were grown at 22° C. in a 16h–8h light-dark cycle with light intensity approximately 65 $\mu Em^{-2}s^{-1}$. After 5 days the seedlings were taken under sterile conditions and the hypocotyls excised and cut into pieces of about 4 mm in length. The hypocotyl segments were placed on a feeder plate or without the feeder layer on top of a filter paper on the solidified B5 0/1/1 or B5 0/1/0 medium. B5 0/1/0 medium contains B5 salts and vitamins (Gamborg, Miller and Ojima, *Experimental Cell Res.* (1968) 50:151–158), 3% sucrose, 2,4-dichlorophenoxyacetic acid (1.0 mg/l), pH adjusted to 5.8, and the medium is solidified with 0.6% Phytagar; B5 0/1/1 is the same with the addition of 1.0 mg/l kinetin. Feeder plates were prepared 24 hours in advance by pipetting 1.0 ml of a stationary phase tobacco suspension culture (maintained as described in Fillatti et al., *Molecular General Genetics* (1987) 20.6:192–199) onto B5 0/1/0 or B5 0/1/1 medium. Hypocotyl segments were cut and placed on feeder plates 24 hours prior to Agrobacterium treatment.

Agrobacterium tumefaciens (strain EHA101x948) was prepared by incubating a single colony of Agrobacterium in MG/L broth at 30° C. Bacteria were harvested 16 hours later and dilutions of $10^8$ bacteria per ml were prepared in MG/L broth. Hypocotyl segments were inoculated with bacteria by placing the segments in an Agrobacterium suspension and allowing them to sit for 30–60 minutes, then removing and transferring to Petri plates containing B5 0/1/1 or 0/1/0 medium (0/1/1 intends 1 mg/l2,4-D and 1 mg/l kinetin and 0/1/0 intends no kinetin). The plates were incubated in low light at 22° C. The co-incubation of bacteria with the hypocotyl segments took place for 24–48 hours. The hypocotyl segments were removed and placed on B5 0/1/1 or 0/1/0 containing 500 mg/l carbenicillin (kanamycin sulfate at 10, 25, or 50 mg/l was sometimes added at this time) for 7 days in continuous light (approximately 65 $\mu Em^{-2}S^{-1}$) at 22° C. The segments were transferred to B5 salts medium containing 1% sucrose, 3 mg/l benzylamino purine (BAP) and 1 mg/l zeatin. This was supplemented with 500 mg/l carbenicillin, 10, 25, or 50 mg/l kanamycin sulfate, and solidified with 0.6% Phytagar (Gibco). Thereafter, explants were transferred to fresh medium every two weeks.

After one month green shoots developed from green calli which were selected on media containing kanamycin. Shoots continued to develop for three months. The shoots were cut from the calli when they were at least 1 cm high and placed on B5 medium with 1% sucrose, no added growth substances, 300 mg/l carbenicillin, and solidified with 0.6% phytagar. The shoots continued to grow and several leaves were removed to test for neomycin phosphotransferase II (NPTII) activity. Shoots which were positive for NPTII activity were placed in Magenta boxes containing B5 0/1/1 medium with 1% sucrose, 2 mg/l indolebutyric acid, 200 mg/l carbenicillin, and solidified with 0.6% Phytagar. After a few weeks the shoots developed roots and were transferred to soil. The plants were grown in a growth chamber at 22° C. in a 16–8 hours light-dark cycle with light intensity 220 $\mu Em^{-2}s^{-1}$ and after several weeks were transferred to the greenhouse.

Southern Data

Regenerated *B. napus* plants from cocultivations of *Agrobacterium tumefaciens* EHA101 containing pCGN948 and *B. napus* hypocotyls were examined for proper integration and embyro-specific expression of the spinach leaf ACP gene. Southern analysis was performed using DNA isolated from leaves of regenerated plants by the method of Dellaporta et al. (*Plant Mol. Biol. Rep.* (1983) 1:19–21) and purified once by banding in CsCl. DNA (10 µg) was digested with the restriction enzyme EcoRI, electrophoresed on a 0.7% agarose gel and blotted to nitrocellulose (see Maniatis et al., (1982) supra.). Blots were probed with pCGN945 DNA containing 1.8 kb of the spinach ACP sequence or with the EcoRI-HindIII fragment isolated from pCGN936c (made by transferring the HindIII-EcoRI fragment of pCGN930 into pCGN566) containing the napin 5' sequences labeled with $^{32}$P-dCTP by nick translation (described by the manufacturer, BRL Nick Translation Reagent Kit, Bethesda Research Laboratories, Gaithersburg, Md.). Blots were prehybridized and hybridized in 50% formamide, 10×Denhardt's, 5×SSC, 0.1% SDS, 5 mM EDTA, 100 µg/ml calf thymus DNA and 10% dextran sulfate (hybridization only) at 42° C. (Reagents described in Maniatis et al., (1982) supra.) Washes were in 1×SSC, 0.1% SDS, 30 min and twice in 0.1×SSC, 0.1% SDS 15 min each at 55° C.

Autoradiograms showed two bands of approximately 3.3 and 3.2 kb hybridized in the EcoRI digests of DNA from four plants when probed with the ACP gene (pCGN945) indicating proper integration of the spinach leaf ACP construct in the plant genome since 3.3 and 3.2 kb EcoRI fragments are present in the T-DNA region of pCGN948. The gene construct was present in single or multiple loci in the different plants as judged by the number of plant DNA-construct DNA border fragments detected when probed with the napin 5' sequences.

Northern Data

Expression of the integrated spinach leaf ACP gene from the napin promoter was detected by Northern analysis in seeds but not leaves of one of the transformed plants shown to contain the construct DNA. Developing seeds were collected from the transformed plant 21 days postanthesis. Embryos were dissected from the seeds and frozen in liquid nitrogen. Total RNA was isolated from the seed embryos and from leaves of the transformed plant by the method of Crouch et al., (1983) supra., electrophoresed on formaldehyde-containing 1.5% agarose gels as described (Shewmaker et al., Virology (1985) 140:281–288) and blotted to nitrocellulose (Thomas, *Proc. Natl. Acad. Sci. USA* (1980) 77:5201–5205). Blots were prehybridized, hybridized, and washed as described above. The probe was an isolated PstI-BamHI fragment from pCGN945 containing only spinach leaf ACP sequences labeled by nick translation.

An RNA band of ~0.8 kb was detected in embryos but not leaves of the transformed plant indicating seed-specific expression of the spinach leaf ACP gene.

EXAMPLE II

Construction of B. Campstris Napin Promoter Cassette

A BglII partial genomic library of *B. campestris* DNA was made in the lambda vector Charon 35 using established protocols (Maniatis et al., (1982) supra). The titer of the amplified library was ~1.2×10$^9$ phage/ml. Four hundred thousand recombinant bacteriophage were plated at a density of 10$^5$ per 9×9 in. NZY plate (NZYM as described in Maniatis et al., (1982) supra) in NZY+10 mM MgSO$_4$+0.9% agarose after adsorption to DH1 *E. coli* cells (Hanahan, *Mol. Biol.* (1983) 166:557) for 20 min at 37° C. Plates were incubated at 37° C. for ~13 hours, cooled at 4° C. for 2.5 hours and the phage were lifted onto Gene Screen Plus (New England Nuclear) by laying precut filters over the plates for approximately 1 min and peeling them off. The adsorbed phage DNA was immobilized by floating the filter on 1.5M NaCl, 0.5M NaOH for 1 min., neutralizing in 1.5 M NaCl, 0.5 M Tris-HCl, pH 8.0 for 2 min and 2XSSC for 3 min. Filters were air dried until just damp, prehybridized and hybridized at 42° C. as described for Southern analysis. Filters were probed for napin-containing clones using an XhoI-SalI fragment of the cDNA clone BE5 which was isolated from the *B. campestris* seed cDNA library described using the probe pN1 (Crouch et al., (1983) supra). Three plaques were hybridized strongly on duplicate filters and were plaque purified as described (Maniatis et al., (1982) supra).

One of the clones named lambda CGN1–2 was restriction mapped and the napin gene was localized to overlapping 2.7 kb XhoI and 2.1 kb SalI restriction fragments. The two fragments were subcloned from lambda CGN1–2 DNA into pCGN789 (a pUC based vector the same as pUC119 with the normal polylinker replaced by the synthetic linker (SEQ ID NO: 13) –5' GGAATTCGTCGACAGATCTCTGCAG CTCGAGGGATCCAAGCTT 3'(which represents the polylinker EcoRI, SalI, BiII, PstI, XhoI, BamHI, HindIII). The identity of the subclones as napin was confirmed by sequencing. The entire coding region sequence as well as extensive 5' upstream and 3' downstream sequences were determined (FIGS. 2A, 2B, 2C, 2D, 2E, 2F, 2G, 2H, 2I and 2J). The lambda CGN1–2 napin gene is that encoding the mRNA corresponding to the BE5 cDNA as determined by the exact match of their nucleotide sequences.

An expression cassette was constructed from the 5'-end and the 3'-end of the lambda CGN1–2 napin gene as follows in an analogous manner to the construction of pCGN944. The majority of the napin coding region of pCGN940 was deleted by digestion with SalI and religation to form pCGN1800. Single-stranded DNA from pCGN1800 was used in an in vitro mutagenesis reaction (Adelman et al., DNA (1983) 2:183–193) using the synthetic oligonucleotide (SEQ ID NO: 14) 5 ' GCTTGTTCGCCATGGATATCTT CTGTATGTTC 3'. This oligonucleotide inserted an EcoRV and an Nco1 restriction site at the junction of the promoter region and the ATG start codon of the napin gene. An appropriate mutant was identified by hybridization to the oligonucleotide used for the mutagenesis and sequence analysis and named pCGN1801.

A 1.7 kb promoter fragment was subcloned from pCGN1801 by partial digestion with EcoRV and ligation to pCGN786 (a pCGN566 chloramphenicol based vector with the synthetic linker described above in place of the normal polylinker) cut with EcoRI and blunted by filling in with DNA Polymerase I Klenow fragment to create pCGN1802. 3' sequences from the lambda CGN1-2 napin gene were added to XhoI-HindIII digested pCGN1802 from pCGN941 digested with XhoI and HindIII. The resulting clone, pCGN1803, contains approximately 1.6 kb of napin 3'-sequences as well as promoter sequences, but a 326 nucleotide HindIII fragment normally found at the 3'-end of lambda CGN1–2 is inserted opposite to its natural orientation. As a result, there are two HindIII sites in pCGN1803. This reversed fragment was removed by digestion of pCGN1803 with HindIII. Following religation, a clone was selected which now contained only approximately 1.25 kb of the original 1.6 napin 3'-sequence. This clone, pCGN1808, is the lambda CGN1–2 expression cassette and contains 1.725 kb of napin promoter sequence, and 1.265 kb of napin 3' sequences with the unique cloning sites SalI, BglI, PstI, and XhoI in between. Any sequence that requires seed-specific transcription or expression in Brassica, for example, a fatty acid gene, can be inserted in this cassette in a manner analogous to that described for spinach leaf ACP and the *B. napus* napin cassette (see Example I. )

Example III

Other seed-specific promoters may be isolated from genes encoding proteins involved in seed triacylglycerol synthesis, such as acyl carrier protein from Brassica seeds. Immature seed were collected from *Brassica campestris* cv. "R-500," a self-compatible variety of turnip rape. Whole seeds were collected at stages corresponding approximately to 14 to 28 days after flowering. RNA isolation and preparation of a cDNA bank was as described above for the isolation of a spinach ACP cDNA clone except the vector used was pCGN565. To probe the cDNA bank, the oligonucleotide (SEQ ID NO.75) (5') -ACTTTCTCAACTGTCTCTGGTT-TAGCAGC-(3') was synthesized using an Applied Biosystems DNA Synthesizer, model 380A, according to manufacturer's recommendations. This synthetic DNA molecule will hybridize at low stringencies to DNA or RNA sequences coding for the amino acid sequence (SEQ ID NO: 16) (ala-ala-lys-pro-glu-thr-val-glu-lys-val). This amino acid sequence has been reported for ACP isolated from seeds of *Brassica napus* (Slabas et al., 7th International Symposium of the Structure and Function of Plant Lipids, University of California, Davis, Calif., 1986); ACP from B. campestris seed is highly homologous. Approximately 2200 different cDNA clones were analyzed using a colony hybridization technique (Taub and Thompson, *Anal. Blochem.* (1982) 12.6.:222–230) and hybridization conditions corresponding to Wood et al. (*Proc. Natl. Acad. Sci.* (1985) 82:1585–1588). DNA sequence analysis of two cDNA clones showing obvious hybridization to the oligonucleotide probe indicated that one, designated pCGN1 Bcs, indeed coded for an ACP-precursor protein by the considerable homology of the encoded amino acid sequence with ACP proteins described from *Brassica napus* ( Slabas et al., 1980 supra). Similarly to Example II, the ACP cDNA clone, pCGN1Bcs, was used to isolate ACP genomic clones containing the regulatory information for expression of ACP during triacylglyceride synthesis in the seeds. DNA was isolated from *B. campestris* cv. R500 young leaves by the procedure of Scofield and Crouch (*J. Biol. Chem.* (1987) 262: 12202–12208). A Sau3A partial genomic library of the *B. campestris* DNA was made in the lambda vector Embl 3 (Stratagene, San Diego, Calif.) using established protocols (Maniatis et al., (1982) supra) and manufacturer's instructions. The titer of the library was ~1.0×10$^8$ phage/ml. Six hundred thousand recombinant bacteriophage were plated and screened as described in Example II with the exception that the *E. coli* host cells used were strain P2392 (Stratagene, San Diego, Calif.). Filters were prehybridized and hybridized at 42° C. in 25 ml each of hybridization buffer containing 50% formamide, 10×Denhardt's, 5X SSC, 5 mM EDTA, 0.1% SDS, and 100 µg/ml denatured salmon sperm DNA (reagents described in Maniatis et al., (1982) supra). The probe used in these hybridizations was 0.2 µg of a nick-translated 530 base pair BglII-DraI fragment of pCGN1 Bcs, the *B. campestris* ACP cDNA clone described above. Six plaques were hybridized strongly on duplicate filters after washing the filters at 55° C. in 0.1× SSC/0.2% SDS, and were plaque-purified as described (Maniatis et al., (1982) supra).

Figure 3B:
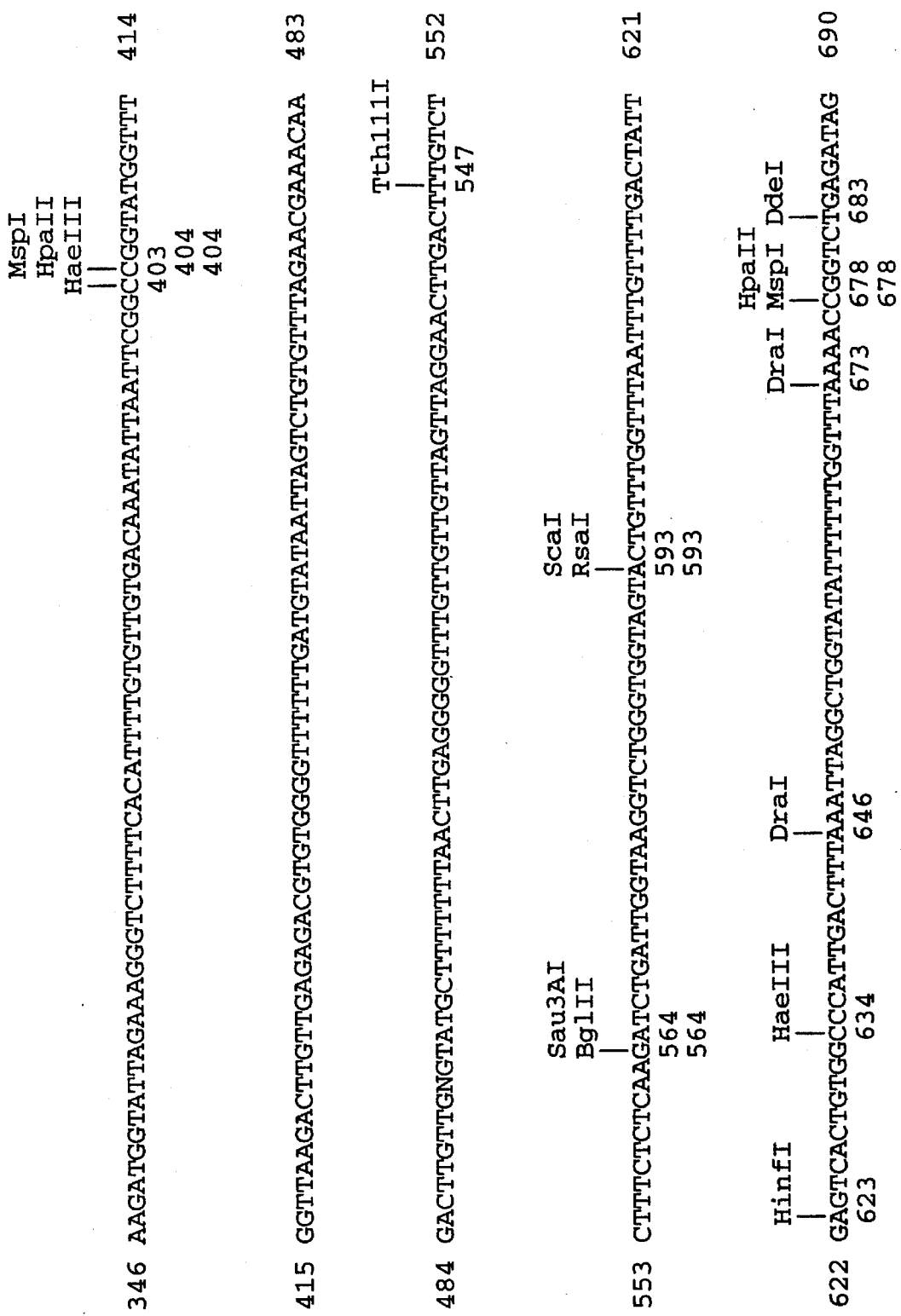
Figure 3E:
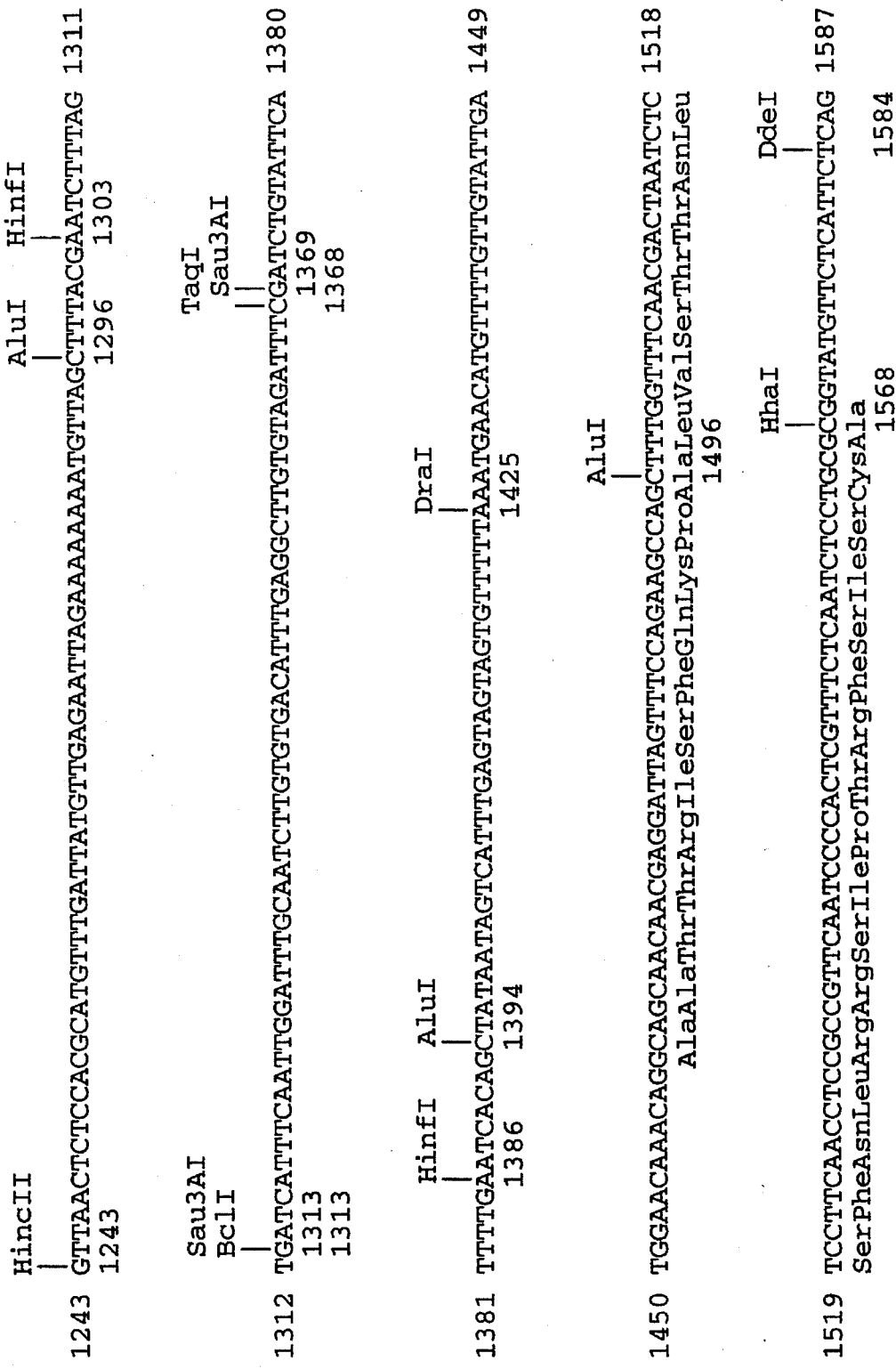

Restriction analysis followed by Southern hybridization was performed on some of the clones using the hybridization conditions and radiolabeled probe described above. One clone, Bcg4—4, contains the ACP gene on two overlapping restriction fragments, an ~5.1 kb SstI fragment and an ~1.2 kb HindIII fragment. These restriction fragments were subcloned into the cloning vector pCGN565. The DNA sequence of some regions of the subclones verified by homology that Bcg4—4 is an ACP gene. The sequence also shows that this particular ACP gene is expressed in plants, as the sequence in the coding region matches exactly the sequence of the pCGN1 Bcs ACP cDNA except for three regions. These regions are believed to be intervening sequences, a common element of eukaryotic genes that is spliced out during processing of mRNA (Padgett et al., *Ann. Rev. Biochem.* (1986) 55:1119–1150). Further restriction mapping of the SstI subclone identified an XhoI fragment containing ~1.5 kb of 5' sequence upstream from the XhoI site near the 5' end of the pCGN1 Bcs cDNA clone. This XhoI fragment was subcloned in opposite orientations in the cloning/sequencing vector Blue-script +(Stratagene, San Diego, Calif.) and the clones were designated pCGN1941 and pCGN1941'. DNA sequencing of 1 kb of the DNA upstream of the coding region was completed. Also, the complete sequence of the 1.2 kb HindIII subclone described above was determined. The DNA sequence derived from the clones described above is shown in FIGS. 3A, 3B, 3C, 3D and 3E. Additional sequences at the 3' end of the ACP gene were subcloned on an ~1.6 kb SstI-BglII fragment into Bluescript+and Bluescript– (clones are designated pCGN1940 and pCGN1940'). The SstI site in these clones is the one found at the 3' end of the ACP coding region of pCGN1 Bcs.

An expression cassette can be constructed from the 5' upstream sequences and 3' downstream sequences of Bcg4—4 as follows. The pCGN1941 XhoI subclone is used for the 5' regulatory region. This clone contains the XhoI insert in the opposite orientation of the lacZ gene. The 3' regulatory region is altered to allow cloning as a PstI-BglII fragment into pCGN565 by oligonucleotide site-directed mutagenesis. Single-stranded DNA is made from pCGN1940 and altered by mutagenesis as described (Adelman et al., supra) with the synthetic oligonucleotide (SEQ ID NO: 12) 5 ' CTTAAGAAGTAACCCGGGCTG-CAGTTTTAGTATTAAGAG 3'. This oligonucleotide provides SmaI and PstI restriction sites just after the TAA stop codon of the pCGN1Bcs cDNA. The PstI-BglII 3' fragment is then cloned into the PstI and BamHI sites (the BamHI restriction site is destroyed in this process) of pCGN565. The resulting clone is digested with PstI and SmaI, and the fragment inserted into the corresponding sites in pCGN1941 (described above) in the same orientation as the 5' region. The resulting clone comprises the ACP expression cassette with PstI, EcoRI, and EcoRV sites available between the 5' and 3' regulatory regions for the cloning of genes to be expressed under the regulation of these ACP gene regions.

EXAMPLE IV

Isolation of Seed-specific cDNA Clone, EA9

Ninety-six clones from the 14–28 day postanthesis *B. campestris* seed cDNA library (described in the previous example) were screened by dot blot hybridization of miniprep DNA on Gene Screen Plus nylon filters ( NEN Research Products, Boston, Mass.). The probes used were radioactively labeled first-strand synthesis cDNAs made from the day 14–28 postanthesis seed mRNA or from *B. campestrls* leaf mRNA. Clones which hybridized strongly to seed cDNA and little or not at all to leaf cDNA were catalogued. A number of clones were identified as representing the seed storage protein napin by cross-hybridization with an XhOI-SalI fragment of pNI (Crouch et al. , (1983) supr$_a$), a *B. napus* napin cDNA. One of these napin clones, BE5, was used in Example II to identify a *B. campestris* genomic clone as a source of an embryo-specific promoter.

Another abundant class of cDNA clones were those represented by a clone designated EA9. EA9 cross-hybridized to seven other cDNA clones of 600 cDNAs screened by dot blot hybridization and was highly expressed in seeds and not in leaves. Northern blot analysis of mRNA isolated from day 14 postanthesis whole seed, and day 21 and 28 postanthesis embryos using a 700 bp EcoRI fragment of EA9 (see below) as a probe shows that EA9 is highly expressed at day 14 and expressed at a much lower level at day 21 and day 28 postanthesis. Because the embryo is so small at day 14, it was suspected that the predominant expression of EA9 might be in a tissue other than the embryo. Total RNA was isolated (Crouch et al., (1983) supra) from whole seed (14, 15, 17 and 19 days postanthesis), seed coats (day 14 and day 21 postanthesis) and embryos (day 21 postanthesis). Twenty-five μg of each sample were analyzed by Northern blot analysis as described in Example I. The probe used was a 0.7 kb EcoRI DNA fragment isolated from the EA9 cDNA and labeled by nick-translation. The results of the Northern analysis showed the EA9 RNA was detected in whole seed at all times tested and in seed coats, but not in the embryo. A separate Northern analysis of whole seed RNA from days 13 through day 31 postanthesis (in two day intervals) indicated that EA9 was highly expressed between days 13 to 21 but was barely detectable by day 27 postanthesis.

In Situ Hybridization

Seed-coat specific expression of EA9 was confirmed by in situ hybridization analysis. Day 14 and 21 postanthesis whole seeds of *B. campestris* were fixed in a 4% paraformaldehyde phosphate buffered saline (PBS) solution. The tissue was then dehydrated through a graded tertiary-butyl alcohol (TBA) series, infiltrated with paraplast and cast into paraffin blocks for sectioning (Berlyn and Miksche, *Botanical Microtechnique and Cytochemistry* (1976), Iowa State University Press). Five μm longitudinal sections of the embedded seeds (one cell-layer thickness) were generated on a Reichert Histostat rotary microtome. The paraffin ribbons containing the seed sections were then affixed to gelatin-chrome alum subbed slides (Berlyn and Miksche, (1976) supra).

Single-stranded radiolabeled RNA probes were made using the Riboprobe reaction system (Promega, Madison, Wis.). This system utilizes a vector which is derived from pUC12 and contains a bacteriophage SP6 promoter which lies immediately upstream from an M13 polylinker. First, the 700 bp EcoRI fragment was isolated from EA9 and subcloned into the polylinker region of the riboprobe vector in both orientations (sense and anti-sense). To generate a template for the transcription run-off transcription reactions, the recombinant plasmids were propagated, purified, and linearized with HindIII. The templates were then incubated in a reaction mixture containing the SP6 RNA polymerase, triphosphates and $^{35}$S-UTP (as described by the manufacturer). After adding RQ DNase (Promega), the labeled RNAs were run over Boehringer pre-packed Sephadex spin columns to remove unincorporated triphosphates.

The slides containing the sectioned seeds were hybridized with the radiolabeled sense and anti-sense RNA transcripts of EA9 according to the methods of Singer et al. (*Biotechniques* (1986) 4:230–241 ) and Taylor and Martineau (*Plant. Physiol.* (1986) 82.:613–618). The hybridized slides were then treated with nuclear track emulsion NTB-3, (Eastman Kodak Company, Kodak Materials for Light Microscope Autoradiography, 1986) sealed in a light-tight box and exposed for 4 weeks at 5°–10° C. After bringing the slides to room temperature they were developed in D-19 developer (Eastman Kodak Company), rinsed, fixed and dehydrated through a graded alcohol series. Cover slips were mounted with cytoseal (VWR Scientific).

Hybridization of the radiolabeled anti-sense EA9 riboprobe was seen only in the seed coat tissue of both day 14 and 21 seeds. No hybridization of the radiolabeled sense EA9 riboprobe was seen in any seed tissues.

DNA Sequence and Gene Copy Number

The restriction map and sequence of the EA9 cDNA clone have been determined (FIGS. 4A, 4B, 4C and 4D). Identification of a polyadenylation signal (Proudfoot and Brownlee, *Nature* (1976) 263:211–214) and of polyA tails at the 3'-end of EA9 indicated the orientation of the cDNA clone and the direction of transcription of the mRNA. The function of the encoded protein is unknown at this time.

EA9 is a member of a small gene family as shown by Southern blot analysis. DNA was isolated from *B. campestris* leaves (as described in Example I, Southern analysis), digested with either BamHI, BglII or HindIII and probed with a labeled fragment of EA9. Three fragments of genomic DNA hybridized in both BamHI and BglII digests. Only 2 bands hybridized in the HindIII digest. The data suggests that the EA9 family comprises between one and three genes.

The sequence of EA9 is used to synthesize a probe which identifies a unique class of Brassica seed-specific genes from a genomic library in the manner described in Examples II and III. The regulatory sequences of these genes is used to construct an expression cassette similar to those described for the napin genes, with the EA9 construct directing seed coat specific expression of any gene inserted in it.

Other Examples

Other seed-specific genes may also serve as useful sources of promoters. cDNA clones of cruciferin, the other major seed storage protein of *B. napus,* have been identified (Simon et al., 1985) supra) and could be used to screen a genomic library for promoters.

Without knowning the specific functions, yet other cDNA clones can be classified as to their level of expression in seed tissues, their timing of expression (i.e., when postanthesis they are expressed) and their approximate representation (copy number) in the *B. campestris* genome. Clones fitting the criteria necessary for expressing genes related to fatty acid synthesis or other seed functions can be used to screen a genomic library for genomic clones which contain the 5' and 3' regulatory regions necessary for expression. The non-coding regulatory regions can be manipulated to make a tissue-specific expression cassette in the general manner described for other genes in previous examples.

It is evident from the above results, that transcription or expression can be obtained specifically in seeds, so as to permit the modulation of phenotype or change in properties of a product of seed. It is found that one can use transcriptional initiation regions associated with the transcription of sequences in seeds in conjunction with sequences other than the normal sequence to produce endogenous or exogenous proteins or modulate the transcription or expression of nucleic acid sequences. In this manner, seeds can be used to produce novel products, to provide for improved protein compositions, to modify the distribution of fatty acid, and the like.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A Brassica plant comprising:
a DNA construct comprising, in the 5' to 3' direction of transcription, a transcriptional initiation region from a gene that encodes a product preferentially expressed in a plant seed cell as compared to other plant cells, a DNA sequence of interest other than the native coding sequence of said gene, and a transcriptional termination region, wherein said gene is a napin gene, an acyl carrier protein gene or an EA9 gene.

2. The Brassica plant according to claim 1, wherein said DNA construct further comprises a translational initiation region immediately downstream of said transcriptional initiation region.

3. The Brassica plant according to claim 1 wherein said DNA sequence of interest comprises an open reading frame that encodes a peptide.

4. The Brassica plant according to claim 1, wherein said DNA sequence of interest is complementary to an mRNA endogenous to a plant seed cell.

5. The Brassica plant according to claim 1, wherein said transcriptional initiation region is from a gene expressed in a Brassica seed cell.

6. The Brassica plant according to claim 1, wherein said transcriptional initiation region is obtainable from a DNA selected from the group consisting of DNA depicted in SEQ ID NO:1, SEQ ID NO:2, SEQ ID NO:4 and SEQ ID NO:9.

7. The Brassica plant according to claim 1, wherein said transcriptional termination region is native with the transcriptional initiation region.

8. A Brassica seed comprising:
   a DNA construct comprising, in the 5' to 3' direction of transcription, a transcriptional initiation region from a gene that encodes a product preferentially expressed in a plant seed cell as compared to other plant cells, a DNA sequence of interest other than the native coding sequence of said gene, and a transcriptional termination region, wherein said gene is a napin gene, an acyl carrier protein gene or an EA9 gene.

9. The Brassica seed according to claim 8 wherein said DNA construct further comprises a translational initiation region immediately downstream of said transcriptional initiation region.

10. Brassica seed according to claim 8, wherein said DNA sequence of interest comprises an open reading frame that encodes a peptide.

11. The Brassica seed according to claim 8, wherein said DNA sequence of interest is complementary to an mRNA endogenous to a plant seed cell.

12. The Brassica seed according to claim 8, wherein said transcriptional initiation region is from a gene expressed in a Brassica seed cell.

13. The Brassica see according to claim 8, wherein said transcriptional initiation region is obtainable from a DNA selected from the group consisting of DNA depicted in SEQ ID NO:1, SEQ ID NO:2, SEQ ID NO:4 and SEQ ID NO:9.

14. The Brassica seed according to claim 8, wherein said transcriptional termination region is native with the transcriptional initiation region.

* * * * *